(12) United States Patent
Suzuki et al.

(10) Patent No.: US 12,171,911 B2
(45) Date of Patent: Dec. 24, 2024

(54) IMPLANTABLE CELL DRESSING FOR TREATMENT OF DISEASE

(71) Applicants: QUEEN MARY UNIVERSITY OF LONDON, London (GB); KANEKA CORPORATION, Osaka (JP)

(72) Inventors: Ken Suzuki, London (GB); Nobuyoshi Umeda, Kobe (JP)

(73) Assignees: QUEEN MARY UNIVERSITY OF LONDON, London (GB); KANEKA CORPORATION, Osaka (JP)

(*) Notice: Subject to any disclaimer, the term of this patent is extended or adjusted under 35 U.S.C. 154(b) by 963 days.

(21) Appl. No.: 16/971,430

(22) PCT Filed: Mar. 22, 2019

(86) PCT No.: PCT/GB2019/050819
§ 371 (c)(1),
(2) Date: Aug. 20, 2020

(87) PCT Pub. No.: WO2019/180454
PCT Pub. Date: Sep. 26, 2019

(65) Prior Publication Data
US 2021/0085828 A1    Mar. 25, 2021

(30) Foreign Application Priority Data

Mar. 22, 2018 (GB) .................................. 1804572
Aug. 7, 2018 (GB) .................................. 1812837

(51) Int. Cl.
*A61L 27/38* (2006.01)
*A61L 27/20* (2006.01)
(Continued)

(52) U.S. Cl.
CPC .......... *A61L 27/3834* (2013.01); *A61L 27/20* (2013.01); *A61L 27/222* (2013.01); *A61L 27/225* (2013.01); *A61L 27/227* (2013.01); *A61L 27/58* (2013.01)

(58) Field of Classification Search
CPC .................................................. A61L 27/3834
See application file for complete search history.

(56) References Cited

U.S. PATENT DOCUMENTS 7,189,410 B1 * 3/2007 Drohan .................. A61K 31/43
514/3.3
2002/0042373 A1 * 4/2002 Carney ................. A61L 27/227
514/17.1
(Continued)

FOREIGN PATENT DOCUMENTS

CN   106823014 A   6/2017
EP   2 500 042 A1  9/2012
(Continued)

OTHER PUBLICATIONS

Barbara A. Christy et al. "Procoagulant activity of human mesenchymal stem cells." Journal of Trauma Acute Care Surgery, vol. 83, No. 1, Supplement 1, 2017, pp. S164-S169. (Year: 2017).*
(Continued)

*Primary Examiner* — Isaac Shomer
(74) *Attorney, Agent, or Firm* — Birch, Stewart, Kolasch & Birch, LLP

(57) ABSTRACT

The present invention provides a multilayer matrix comprising at least two layers in which the first layer comprises a bioresorbable material and the second layer comprises a bioadhesive material, wherein the second layer contains cells. A method for producing a multilayer matrix and the use of a multilayer matrix are also provided.

14 Claims, 16 Drawing Sheets

(51) Int. Cl.
A61L 27/22 (2006.01)
A61L 27/58 (2006.01)

(56) References Cited

U.S. PATENT DOCUMENTS

| | | | |
|---|---|---|---|
| 2003/0176315 A1* | 9/2003 | Barry | A61P 19/10 435/7.1 |
| 2008/0107710 A1 | 5/2008 | Geistlich et al. | |
| 2009/0202495 A1 | 8/2009 | Bhatia et al. | |
| 2010/0055078 A1 | 3/2010 | Hughes-Fulford | |
| 2011/0071498 A1 | 3/2011 | Hakimimehr et al. | |
| 2011/0081326 A1* | 4/2011 | Hantash | C12N 5/0656 435/325 |
| 2011/0256183 A1* | 10/2011 | Frank | C12N 5/0671 435/395 |
| 2012/0282318 A1 | 11/2012 | Nishida et al. | |
| 2013/0259854 A1* | 10/2013 | Rezaie | A61P 41/00 424/94.64 |
| 2014/0341865 A1 | 11/2014 | Jeon et al. | |
| 2015/0231312 A1 | 8/2015 | Sawa et al. | |
| 2015/0250824 A1* | 9/2015 | Ma | C12N 5/0607 435/375 |
| 2015/0252322 A1* | 9/2015 | Nain | D01D 5/04 435/396 |
| 2016/0051722 A1 | 2/2016 | Lee et al. | |
| 2016/0108109 A1 | 4/2016 | Taniyama et al. | |
| 2017/0055993 A1* | 3/2017 | Harris | A61B 17/07207 |
| 2017/0191118 A1* | 7/2017 | Wei | G01N 33/5438 |
| 2019/0270964 A1* | 9/2019 | Hayashi | C12N 5/0668 |

FOREIGN PATENT DOCUMENTS

| | | |
|---|---|---|
| EP | 3 092 989 A1 | 11/2016 |
| JP | 2001-321157 A | 11/2001 |
| JP | 2007-215519 A | 8/2007 |
| JP | 2015-192640 A | 11/2015 |
| JP | 2016-518912 A | 6/2016 |
| JP | 2017-201895 A | 11/2017 |
| WO | WO 02/45767 A1 | 6/2002 |
| WO | WO 03/009783 A1 | 2/2003 |
| WO | WO 03/093433 A2 | 11/2003 |
| WO | WQ 2011/035020 A1 | 3/2011 |
| WO | WO 2011/058813 A1 | 5/2011 |
| WO | WO 2014/136910 A1 | 9/2014 |
| WO | WO-2018092769 A1 * 5/2018 ............. A61K 35/50 |

OTHER PUBLICATIONS

Alexandru-Cristian Tuca et al. "Comparison of Matrigel and Matriderm as a carrier for human amnion-derived mesenchymal stem cells in wound healing." Placenta, vol. 48, 2016, pp. 99-103. (Year: 2016).*
Alex J.T. Hyatt, Difei Wang, Christian van Oterendorp, James W. Fawcett, and Keith R. Martin. "Mesenchymal stromal cells integrate and form longitudinally-alignedlayers when delivered to injured spinal cord via a novel fibrin scaffold." Neuroscience Letters, vol. 569, 2014, pp. 12-17. (Year: 2014).*
Sang-Hyug Park, Byung Hyune Choi, So Ra Park, and Byoung-Hyun Min. "Chondrogenesis of Rabbit Mesenchymal Stem Cells in Fibrin/Hyaluronan Composite Scaffold In Vitro." Tissue Engineering: Part A, vol. 17, Nos. 9 and 10, 2011, pp. 1277-1286. (Year: 2011).*
Arana et al., "Epicardial delivery of collagen patches with adipose-derived stem cells in rat and minipig modes of chronic myocardial infarction," Biomaterials (2014), vol. 35, pp. 143-151.
Bel et al., "A new absorbable collagen membrane to reduce adhesions in cardiac surgery," Interactive CardioVascular and Thoracic Surgery (2010), vol. 10, pp. 213-216.
Campbell, N. G. and K. Suzuki, "Cell Delivery Routes for Stem Cell Therapy to the Heart: Current and Future Approaches," J. Cardiovasc. Transl. Res. (2012), vol. 5, No. 5, pp. 713-726.
Derval et al., "Epicardial deposition of endothelial progenitor and mesenchymal stem cells in a coated muscle patch after myocardial infarction in a murine model," European Journal of Cardio-thoracic Surgery (2008), vol. 34, pp. 248-255.
Donndorf et al., "Intramyocardial bone marrow stem cell transplantation during coronary arty bypass surgery: A meta analysis," J. Thorac. Cardiovasc. Surg. (2011), vol. 142, pp. 911-920.
Escort Clinical Trial—NCT02057900—As available Jul. 2016 (https://clinicaltrials.gov/ct2/history/NCT02057900?A=3&B=3&C=merged#StudyPageTop).
Feng et al., "Epicardial Tachosil Patch Repair of Ventricular Rupture in a 90-Year-Old After Mitral Valve Replacement," The Ann, Thorac. Surg. (2016), vol. 101, No. 6, pp. 2361-2363.
Fukushima et al., "Choice of Cell-Delivery Route for Skeletal Myoblast Transplantation for Treating Post-Infarction Chronic Heart Failure in Rat," PLoS ONE (2008), vol. 3, No. 8, e3071 (11 pages).
Fukushima et al., "Choice of cell-delivery route for successful cell transplantation therapy for the heart," Future Cardiol. (2013), vol. 9. No. 2, 12 pages.
Fukushima et al., "Direct Intramyocardial but not Intracoronary Injection of Bone Marrow Cells Induces Ventricular Arrhythmias in A Rat Chronic Ischemic Heart Failure Model," Circulation (2007), vol. 115, pp. 2254-2261.
Hale et al., "Effect of scaffold dilution on migration of mesenchymal stem cells from fibrin hydrogels," Am. J. Vet. Res. (2012), vol. 73, No. 2, pp. 313-318.
Laflamme et al., "Heart Regeneration," Nature (2011), vol. 473, No. 7347, pp. 326-335.
Menasche, "Cardiac cell therapy: Lessons from clinical trials," J. Mol. Cell. Cardiol. (2011); vol. 50, pp. 258-265.
Mori et al., "Cell Spray Transplantation of Adipose-derived Mesenchymal Stem Cell Recovers Ischemic Cardiomyopathy in a Porcine Model," Transplantation (2018), vol. 102, pp. 2012-2024.
Narita et al., "The use of cell-sheet technique eliminates arrhythmogenicity of skeletal myoblast-based therapy to the heart with enhanced therapeutic effects," Int. J. Cardiol. (2013), vol. 168, pp. 261-269.
Narita et al., "The Use of Scaffold-Free Cell Sheet Technique to Refine Mesenchymal Stromal Cell-based Therapy for Heart Failure," Mol. Ther. (2013), vol. 21, No. 4, pp. 860-867.
Narita, T. and K. Suzuki, "Bone marrow-derived mesenchymal stem cells for the treatment of heart failure," Heart Fail. Rev. (2014), vol. 20, pp. 53-68.
Perin et al., Stem Cell and Gene Therapy for Cardiovascular Disease, Academic Press, Elsevier, 2016, 978-0-12-801888-0, 334-337.
Roura et al., "Postinfarction Functional Recovery Driven by a Three-Dimensional Engineered Fibrin Patch Composed of Human Umbilical Cord Blood-Derived Mesenchymal Stem Cells," Stem Cells Transl. Med. (2015), vol. 4, pp. 956-966.
Suzuki et al., "Targeted Cell Delivery into Infarcted Rat Hearts by Retrograde Intracoronary Infusion: Distribution, Dynamics, and Influence on Cardiac Function," Circulation (2004), vol. 110 [suppl. II] pp. I-225-II-230.
Tano et al., "Epicardial Pplacement of Mmesenchymal Stromal Cell Sheets for the Treatment of Ischemic Cardiomyopathy; In Vivo Proof-of-concept Study," Mol. Ther. (2014), vol. 22, No. 10, pp. 1864-1871.
Willerson et al., "Regenerative Medicine and the Cardiovascular System: A Good Start," Circulation Research (2014), vol. 115, No. 12, pp. 271-278.
Zhang et al., "A PEGylated Fibrin Patch for Mesenchymal Stem Cell Delivery," Tissue Engineering (2006), vol. 12, No. 1, pp. 9-19.
Zhang, "Engineered Tissue Patch for Cardiac Cell Therapy," Curr, Treat. Options Cardiovasc. Med. (2015), vol. 17, No. 8, 12 pages.
Japanese Office Action for corresponding Japanese Application No. 2020-550707, dated Oct. 3, 2023, with English translation.
Kazama, "Basic Research and Clinical Application in Mesenchymal Stem Cells," J. Nihon Univ. Med. Ass., vol. 75, No. 2, 2016, pp. 61-66, with English abstract.

* cited by examiner

Mean±SEM, *p<0.05 vs. Sham group, †p<0.05 vs. TachoSil only group, §p<0.05 vs. MSC IM injection group (one way ANOVA), n=4 in each group.

IMPLANTABLE CELL DRESSING FOR TREATMENT OF DISEASE

The present invention relates to an implantable cell dressing composed of an extracellular matrix-supported, self-adhesive, absorbable biocompatible patch incorporating donor cells for use in medicine, including the treatment of heart disease.

Heart failure remains a major cause of human disability and death, and development of new, efficient, cost-effective strategies for treating heart failure is a high priority. Recent research has shown that transplantation of stem/progenitor cells improves cardiac function of failing hearts (P. Menasche, Cardiac cell therapy: Lessons from clinical trials, *J Mol Cell Cardiol,* 2011; 50, 258-265; M. A. Laflamme et al., Heart regeneration, *Nature* 2011; 473, 326-335). This innovative treatment has been tested in clinical studies using bone marrow-derived cells, mesenchymal stem cells, skeletal myoblasts, cardiac progenitor cells, and so on. However, to date, the therapeutic effect observed in these trials was not as substantial as expected. One of the most important issues underlying this inefficiency is poor donor cell engraftment after cell transplantation, which is largely due to suboptimal cell-delivery route to the heart (N. G. Campbell et al., Cell delivery routes for stem cell therapy to the heart: current and future approaches, *J Cardiovasc Transl Res* 2012; 5(5), 713-726; S. Fukushima et al., Choice of cell-delivery route for successful cell transplantation therapy for the heart. *Future Cardiol.* 2013; 9, 215-227).

Current available cell-delivery methods include intramyocardial, intracoronary and intravenous injection of cell suspensions. All these injection methods, however, result in disappointingly poor donor cell engraftment in the heart. Generally speaking donor cell presence after these injection methods is only <10% at Day 7 and <1% at 28 days (K. Suzuki et al., Targeted cell delivery into infarcted rat hearts by retrograde intracoronary infusion: distribution, dynamics, and influence on cardiac function, *Circulation* 2004; 110, 225-230; S. Fukushima et al., Choice of cell-delivery route for skeletal myoblast transplantation for treating post-infarction chronic heart failure in rat, *PLoS ONE* 2008; 3(8), e3071; S. Fukushima et al., Direct intramyocardial but not intracoronary injection of bone marrow cells induces ventricular arrhythmias in a rat chronic ischemic heart failure model, *Circulation* 2007; 115, 2254-2261). These poor results are mainly because of limited initial retention of injected donor cells in the heart and subsequent poor cell survival. Such poor engraftment of donor cells largely limits the therapeutic efficacy of cell-based therapy. In addition, intramyocardial injection carries a risk of arrhythmia occurrence, while intracoronary injection has a risk of coronary embolism (T. Narita et al., The use of cell-sheet technique eliminates arrhythmogenicity of skeletal myoblast-based therapy to the heart with enhanced therapeutic effects, *Int J Cardiol* 2013; 168, 261-269; S. Fuskushima et al., Direct intramyocardial but not intracoronary injection of bone marrow cells induces ventricular arrhythmias in a rat chronic ischemic heart failure model, *Circulation* 2007; 115, 2254-2261). Thus, development of a more effective and safer delivery method of stem/progenitor cells to the heart is essential for the future success of this emerging treatment for heart failure (T. Narita et al., Bone marrow-derived mesenchymal stem cells for the treatment of heart failure, *Heart Fail Rev* 2015; 20, 53-68; S. Fukushima et al., Choice of cell-delivery route for successful cell transplantation therapy for the heart, *Future Cardiol* 2013, 9(2), 215-227).

To solve this issue, the utility of epicardial placement as opposed to injection has been reported. Cells transplanted via this route by using "cell sheets" generated with temperature-responsive dishes show significantly increased initial retention of 95% (versus 15-30% for intramyocardial injection) at 1 hour of transplantation, which resulted in >5-fold increase of the donor cell presence thereafter (T. Narita et al., The use of cell-sheet technique eliminates arrhythmogenicity of skeletal myoblast-based therapy to the heart with enhanced therapeutic effects, *Int J Cardiol* 2013; 168, 261-269; T. Narita et al., The use of scaffold-free cell sheet technique to refine mesenchymal stromal cell-based therapy for heart failure, *Mol Ther* 2013; 21(4), 860-867; N. Tano et al., Epicardial placement of mesenchymal stromal cell sheets for the treatment of ischemic cardiomyopathy; in vivo proof-of-concept study, *Mol Ther* 2014; 22(10), 1864-1871). The majority of donor cells retained at the epicardial surface, but new vessels were sprouted from the host myocardium by attaching the sheet. As a result, this method achieves augmented cardiac function recovery compared to intramyocardial injection. The cell sheet is, however, technically demanding in production. It is difficult to maintain adequate quality control and the procedure is prolonged up to around 24 hours. The handling of the cell sheets is problematic also as the sheets can be easily torn and long-term storage/transport is difficult. The cell sheets therefore require extensive expertise on the part of medical practitioners which inhibits the use of this method as a generic tool in the clinic.

Simple dribbling of ordinary cell suspension does not allow donor cells to retain on the heart; most of the cells just drop off. It has been reported that the use of hydrogel (such as fibrin glue) enables epicardial placement of stem cells onto the heart surface. However, hydrogel is usually not so stiff that the hydrogel incorporating stem cells are often rubbed out by mechanical contact by surrounding tissue like the pericardium, lung, and the chest wall. In addition, these materials can be a cause of post-operative adhesions, which can cause adverse events.

There is therefore need for a new approach which overcomes these problems in order to enable cell based therapy of diseases to be successful.

The present invention provides the following:

<1> A multilayer matrix comprising at least two layers in which the first layer comprises a bioresorbable material and the second layer comprises a bioadhesive material, wherein the second layer contains cells.

<2> The multilayer matrix according to <1>, wherein the percentage of cells exhibiting positive to CD105, CD73 and CD90 in the cells is 50% or more, and the percentage of cells exhibiting positive to CD45 and CD34 in the cells is 10% or less.

<3> The multilayer matrix according to any of <1> to <2>, wherein the percentage of cells exhibiting positive to CD142 in the cells is 50% or more, and the percentage of cells exhibiting positive to CD106 in the cells is 10% or less.

<4> The multilayer matrix according to any of <1> to <3>, wherein the cells are mesenchymal stem cells.

<5> The multilayer matrix according to any of <1> to <4>, wherein the mesenchymal stem cells are derived from fetal appendage.

<6> The multilayer matrix according to any of <1> to <5>, wherein a cell density comprised in the second layer is $0.3 \times 10^6$ cells/cm$^2$ or more.

<7> The multilayer matrix according to any of <1> to <6>, wherein the administrating area of the multilayer matrix per body weight is 0.1 cm$^2$/kg or more and 6.0 cm$^2$/kg or less.

<8> The multilayer matrix according to any of <1> to <7>, wherein the second layer comprises at least two bioadhesive materials.

<9> The multilayer matrix according to any of <1> to <8>, wherein the bioadhesive material is at least one which is selected from a group consisting of fibrinogen, thrombin, gelatine, laminin, integrin, fibronectin and vitronectin.

<10> The multilayer matrix according to any of <1> to <9>, wherein the bioadhesive material comprises bioresorbable material.

<11> The multilayer matrix according to any of <1> to <10>, wherein the second layer further contains dimethyl sulfoxide and albumin.

<12> The multilayer matrix according to any of <1> to <11>, wherein the bioresorbable material is at least one which is selected from a group consisting of collagen, gelatine, cellulose, cellulose acetate, chitosan, chitin, polylactate, hyaluronic acid, polyglycolic acid and polyvinyl alcohol.

<13> The multilayer matrix according to any of <1> to <12> for use in a method of treatment of a lesion or trauma to a tissue or an organ of a subject.

<14> The multilayer matrix according to <13>, wherein the organ is heart.

<15> The multilayer matrix according to <13>, wherein the tissue is myocardium.

<16> The multilayer matrix according to any of <1> to <15>, wherein the second layer further contains drug(s).

<17> The multilayer matrix according to any of <1> to <16>, wherein a cell suspension is applied to the second layer, and the volume of the cell suspension is 20 μL/cm$^2$ or more and 60 μL/cm$^2$ or less.

<18> The multilayer matrix according to any of <1> to <17>, wherein, after the cells are applied to the multilayer matrix, the survival ratio of the applied cells is maintained to be 70% or more for at least 3 hours.

<19> A multilayer matrix comprising at least two layers in which the first layer comprises a bioresorbable material and the second layer comprises a bioadhesive material, wherein the second layer contains cells, for use in a method of treatment of a lesion or trauma to a tissue or an organ of a subject, wherein prior to applying the multilayer matrix a solution comprising drug(s) is applied to the second layer.

<20> A method for producing a multilayer matrix comprising at least two layers in which the first layer comprises a bioresorbable material and the second layer comprises a bioadhesive material, wherein the second layer contains cells, which comprises steps of;
A) preparing a cell suspension and
B) applying the cell suspension to the second layer of the multilayer matrix.

<21> The method for producing a multilayer matrix according to <20>, wherein the volume of the suspension containing cells is 20 μL/cm$^2$ or more and 60 μL/cm$^2$ or less.

<22> The method for producing a multilayer matrix according to claim <20> or <21>, wherein the cell suspension contains albumin and dimethyl sulfoxide.

<23> The method for producing a multilayer matrix according to claim <22>, wherein the concentration of albumin is 0.5 wt % or more and 8 wt % or less.

<24> The method for producing a multilayer matrix according to claim <22> or <23>, wherein the concentration of dimethyl sulfoxide is 3% or more and 10% or less.

<25> The method for producing a multilayer matrix according to any of <20> to <24>, wherein the cell suspension further contains hydroxyethyl starch.

<26> The method for producing a multilayer matrix according to any of <20> to <25>, wherein the cell concentration of the cell suspension is 5×10$^6$ cells/mL or more and 133×10$^6$ cells/mL or less.

<27> The method for producing a multilayer matrix according to <20> to <26>, wherein the percentage of cells exhibiting positive to CD105, CD73 and CD90 in the cells is 50% or more, and the percentage of cells exhibiting positive to CD45 and CD34 in the cells is 10% or less.

<28> The method for producing a multilayer matrix according to <20> to <27>, wherein the percentage of cells exhibiting positive to CD142 in the cells is 50% or more, and the percentage of cells exhibiting positive to CD106 in the cells is 10% or less.

<29> The method for producing a multilayer matrix according to <20> to <28>, wherein the cells are mesenchymal stem cells.

<30> The method for producing a multilayer matrix according to <20> to <29>, wherein the mesenchymal stem cells are derived from fetal appendage.

<31> The method for producing a multilayer matrix according to <20> to <30>, wherein a cell density when a cell suspension is applied to the multilayer matrix is 0.3×10$^6$ cells/cm$^2$ or more.

<32> The method for producing a multilayer matrix according to <20> to <31>, wherein the administrating area of the multilayer matrix per body weight is 0.1 cm$^2$/kg or more and 6.0 cm$^2$/kg or less.

<33> The method for producing a multilayer matrix according to <20> to <32>, wherein, after the cells are applied to the multilayer matrix, the survival ratio of the applied cells is maintained to be 70% or more for at least 3 hours.

<34> The method for producing a multilayer matrix according to <20> to <33>, wherein the bioresorbable material is at least one which is selected from a group consisting of collagen, gelatine, cellulose, cellulose acetate, chitosan, chitin, polylactate, hyaluronic acid, polyglycolic acid and polyvinyl alcohol.

<35> Use of a multilayer matrix according to <1> for treatment of lesion or trauma to a tissue or organ of a subject.

<36> Use of a multilayer matrix according to <35>, wherein prior to applying the multilayer matrix a suspension comprising cells is applied to the second layer.

<37> Use of a multilayer matrix according to claim 1 for production of an agent for treatment of lesion or trauma to a tissue or organ of a subject.

<38> Use of a multilayer matrix according to <37>, wherein prior to applying the multilayer matrix a suspension comprising cells is applied to the second layer.

<39> A kit of parts which comprises at least cells suspension in a container and a multilayer matrix comprising at least two layers in which the first layer comprises a bioresorbable material and the second layer comprises a bioadhesive material.

<40> The kit of parts according to <39>, wherein the percentage of cells exhibiting positive to CD105, CD73 and CD90 in the cells is 50% or more, and the percentage of cells exhibiting positive to CD45 and CD34 in the cells is 10% or less.

<41> The kit of parts according to <39> or <40>, wherein the percentage of cells exhibiting positive to CD142 in the cells is 50% or more, and the percentage of cells exhibiting positive to CD106 in the cells is 10% or less.

<42> The kit of parts according to any of <39> to <41>, wherein the cells are mesenchymal stem cell.

<43> The kit of parts according to <42>, wherein the mesenchymal stem cells are derived from fetal appendage.

<44> The kit of parts according to any of <39> to <43>, wherein the ratio of the multilayer matrix and the cells is $0.3 \times 10^6$ cells or more per 1 cm$^2$ of multilayer matrix.

<45> The kit of parts according to any of <39> to <44>, wherein the ratio of the multilayer matrix and the cells is 20 µL or more and 60 µL or less per 1 cm$^2$ of multilayer matrix.

<46> The kit of parts according to any of <39> to <45>, wherein the administrating area of the multilayer matrix per body weight is 0.1 cm$^2$/kg or more and 6.0 cm$^2$/kg or less.

<47> The kit of parts according to any of <39> to <46>, wherein the bioresorbable material is at least one which is selected from a group consisting of collagen, gelatine, cellulose, cellulose acetate, chitosan, chitin, polylactate, hyaluronic acid, polyglycolic acid and polyvinyl alcohol.

A multilayer matrix is therefore provided comprising at least two layers in which the first layer comprises a bioresorbable material and the second layer comprises a bioadhesive material, wherein the second layer contains cells. The multilayer matrix may be used in a method of treatment of a lesion or trauma to a tissue or an organ of a subject.

The matrix of the invention may be a multilayer matrix, which is composed of at least one layer made from a bioresorbable material and at least one layer made from a bioadhesive material. But in practice a bilayer may be suitable in many situations. However, additional layers can be added as required to provide further stability or biological activity. For example, layer where a drug for promoting therapy of lesion or trauma is coated can be added.

The first layer comprises a bioresorbable material. The term "bioresorbable material" refers to a material which is degraded and absorbed in living body and provides the matrix with a structure. The structure may be in the form of a scaffold suitable for cell engraftment. This layer may protect the second layer from rubbing or mechanical damage by the surrounding tissues. Suitably, the matrix may be natural or synthetic.

The bioresorbable material is not particularly limited, so long as it does not give harmful effects such as side effects on living body when administered to the living body, and does not deteriorate in living the body environment. The bioresorbable material may be a bioresorbable polymer. Examples of bioresorbable materials include collagen as well as collagen, gelatine and collagen peptide. Examples of bioresorbable material include polysaccharide as well as cellulose, cellulose acetate, oxidized regenerated cellulose, chitosan, chitin and hyaluronic acid. Examples of bioresorbable materials also include those mentioned below as well as polyglactin, polylactic acid, poly glycolic acid, polylactate, polyglycolic acid and polyvinyl alcohol. For example, collagen is preferably used as a bioresorbable material. Any type of collagen may be used as required, for example fibrillar or non-fibrillar collagen. Examples of suitable collagens include Type I, Type II, Type III, Type IV and/or Type V collagen, or mixtures thereof. The collagen may be from any generally suitable source, including human, equine, porcine, bovine, caprine and/or ovine. Gelatine, cellulose, cellulose acetate, chitosan, chitin, polylactate, hyaluronic acid, and polyvinyl alcohol can be preferably used as examples other than collagen.

Optionally, the bioresorbable material may comprise additional components such as preservatives and/or stabilisers. Suitable examples of preservatives and/or stabilisers include albumin, riboflavine, sodium chloride, sodium citrate, and/or L-arginine-hydrochloride, or mixtures thereof.

In one example, the bioresorbable material may comprise equine collagen, human albumin, riboflavine, sodium chloride, sodium citrate, and L-arginine-hydrochloride.

The form of bioresorbable material is desirably sheet-like. Porous sheet such as non-woven cloth or sponge or film-like sheet is preferably used.

The second layer comprises a bioadhesive material. The term "bioadhesive material" refers to a material which exhibits adhesives to organ or tissue. The bioadhesive material provides the matrix with the ability to adhere to a tissue or organ surface when in use. Further, the second layer is preferably a material which shows low toxicity to cells and a bioresorbable material but it is not limited thereto. The bioadhesive material may be composed of extracellular matrix such as fibrinogen, fibronectin, vitronectin and laminin. The bioadhesive material may be composed of cell adhesion molecules such as integrin and selectin. The bioadhesive material may be composed of thrombin and gelatine. Fibrinogen and/or thrombin is preferably used, suitably they are provided in a powdered (suitably anhydrous) form so that the bioadhesive material can be prepared extemporaneously at the time required for use. In practice this means that a medium is applied to the second layer (hereinafter referred to as also a bioadhesive layer) at the time the matrix is required for use. The second layer may comprise at least two bioadhesive materials.

The bioadhesive material may comprise other components such as aprotinin and/or plasminogen.

Further, this multilayer matrix is preferably a material such that the cells to which the material is applied can maintain high survival rate for long period of time. Specifically, when cells applied to the multilayer matrix are maintained at 37° C., it is preferred that 70% or more (more preferably 80% or more, still more preferably 90% or more) of the living cells before application is surviving after at least 3 hours. Further, it is more preferred that 70% or more (more preferably 80% or more, still more preferably 90% or more) of the living cells before application is surviving after at least 6 hours.

In use, the cell suspension applied to the second layer may comprise an aqueous solution and cells with/without drugs. The solution may include saline, phosphate buffered saline, Ringer's solution containing bivalent cation (for example, calcium chloride or magnesium chloride), or a medium. The medium may include HBSS(+), HBSS(−), RPMI, IMEM, DMEM, MEM, and/or cell preservatives, which may be optionally supplemented with serum, plasma or protein-containing solution. A commercially available cryopreservation solution may be preferably used as the solution. For example, CP-1 (manufactured by Kyokuto Pharmaceutical Industry Co., Ltd.), BAMBANKER (manufactured by Lymphotec Corporation), STEM-CELLBANKER (manufactured by Nippon Zenyaku Kogyo Co., Ltd.), ReproCryo RM (manufactured by ReproCell), CryoNovo (Akron Biotechnology, MSC Freezing Solution (manufactured by Biological Industries), CryoStor (manufactured by HemaCare), and the like. The cell preservatives may be a solution of a combination of one or two or more of the above-listed solutions with one or two or more cryopreservatives such as dimethyl sulfoxide, albumin, glycerol, hydroxyethyl starch, or dextran. The concentration of dimethyl sulfoxide is preferably 3 wt % or more, 4 wt % or more, 5 wt % or more. The upper limit of the concentration of dimethyl sulfoxide is 10 wt % or less, 9 wt % or less, 8 wt % or less, 7 wt % or less. The concentration of albumin is preferably 0.5 wt % or more, 1 wt % or more, 2 wt % or more, 3 wt % or more. The upper limit of the concentration of albumin is 8 wt % or less, 7 wt % or less, 6 wt % or less, 5 wt % or less. The concentration of hydroxyethyl starch is preferably 3 wt % or more, 4 wt % or more, 5 wt % or more. The upper limit of the concentration of hydroxyethyl starch is 9 wt % or less, 8 wt % or less, 7 wt % or less. One example of cell preservatives includes a composition of 5 wt % of dimethyl sulfoxide, 6 wt % of hydroxyethyl starch, and 4 wt % of human serum albumin.

In an example of a combination of cell preservatives with multilayer matrix, the cells which are suspended in cell preservative and are supplied in a frozen state are thawed at a clinical practice, and are directly applied to multilayer matrix without a special step of removing cell preservatives by centrifugation and the like. Thus, the period of time for the process for the preparation of a cell coated multilayer matrix can be shortened. For example, the cells can be applied to the multilayer matrix or a patient within 10 minutes.

In an example of a combination of cell preservatives with multilayer matrix, the cells which are suspended in cell preservative and are supplied in a frozen state are thawed at a clinical practice, and are washed with a solution such as saline, phosphate buffered saline, Ringer's solution and medium by centrifugation. Then, the cells are suspended in the solution, prepared to an appropriate cell concentration and applied to multilayer matrix.

The drug(s) to be incorporated in the matrix may be those that protect the host heart or donor cells, activate the function of or enhance the phenotype of donor cells, or induce angiogenesis, anti-inflammation and tissue repair. The drug may therefore include a growth factor (for example IGF-1), an angiogenic factor (for example VEGF), a cytokine (for example IL-10), a chemokine (for example SDF-1), a steroid, an enzyme (for example superoxide dismutase) or combination of these.

The cells to be incorporated in the matrix may be stem cells, progenitor cells, precursor cells, somatic cells, or cell lines, for example induced pluripotent stem (iPS) cells, embryonic stem (ES) cells, mesenchymal stem cells (MSCs), cardiac progenitor cells, cardiomyocytes. The stem cells may be their derivatives, for example progenitor stem cells for a differentiated cell type. The MSCs may be derived from any suitable source, including amnion, chorion, placenta, fetal membrane, bone marrow, cord blood, and adipose tissue. The ES cells may be from a deposited ES cell line. The ES cells may be derived from a parthenogenetically activated oocyte. Suitably, the cells may be allogeneic to the donor. The cells may also be autologous, or in some cases xenogeneic. MSCs may be advantageous over ES cells, iPS cells, cardiac progenitor cells and cardiomyocytes, because MSCs are low immunogenic so that immune response will not be induced when administrating allogeneic MSCs to patient.

The term "Mesenchymal stem cells (MSC)" refers to a stem cell that satisfies the following definitions and is used interchangeably with "mesenchymal stromal cells". As used herein, "mesenchymal stem cells" may be described as "MSC". The definition of mesenchymal stem cells is as follows:
i) adhere to plastic in culture conditions with a standard medium.
ii) positive for surface antigen CD105, CD73 and CD90; negative for CD45, CD34, CD11 b, CD79 alpha and HLA-DR.

The cells to be incorporated in the matrix are to form, for example, cell pellet, cell aggregation, the cell suspension.

The cells in the present invention, the mesenchymal stem cells, are preferably cultured in vitro up to 20 days or more, more preferably 40 days or more, 60 days or more, 80 days or more, 100 days or more. The cells can be cultured with maintaining the normal karyotype and without stopping the growth in the aforementioned terms. The mesenchymal stem cells can be passaged 1 or more, preferably 2 or more, more preferably 3 or more, further preferably 5 or more, further preferably 10 or more. The upper limit of the number of passages is not particularly limited, but it is, for example, 50 times or less, 40 times or less, 30 times or less. The population doubling of mesenchymal stem cells is preferably 10 times or more, more preferably 20 times or more, 30 times or more, 40 times or more, 50 times or more. The upper limit of the population doublings is not particularly limited, but it is, for example, 100 times or less, 80 times or less, 60 times or less. The population doubling is the number of times the cell population has divided during a culture period and is calculated by the following formula; $[\log_{10}$ (the number of cells at the end of culture)$-\log_{10}$ (the number of cells at the start of the culture)$]/\log_{10} 2$.

Fetal appendage-derived MSCs (for example, amnion-derived MSCs) may be advantageous over bone marrow- or adipose tissue-derived MSCs in a greater initial cell-yield and more extensive proliferation ability. Fetal appendage is a clinical waste and thus fetal appendage-derived MSCs are free of invasive biopsy in the patient or volunteering donor and ethical issues. Adipose tissue-derived MSCs may also be preferably used because of a greater initial cell-yield.

The term "fetal appendage" is used to mean a fetal membrane, a placenta, an umbilical cord, and an amniotic fluid. Moreover, the term "fetal membrane" means a gestational sac containing an amniotic fluid surrounding an embryo, and may comprise of an amnion, a chorion and a decidua. Among these, the amnion and the chorion are derived from the embryo. The term "amnion" indicates a transparent thin membrane containing few blood vessels that is positioned on the innermost layer of the fetal membrane. The inner layer of the amnion (which is also referred to as an "epithelial cell layer") is covered with a single layer of epithelial cells having secretory function, and thus, secretes an amniotic fluid. On the other hand, the outer layer of the amnion (which is also referred to as an "extracellular matrix layer" corresponding to the stroma) contains mesenchymal stem cells.

The fetal appendage-derived mesenchymal stem cells may include a cell population including mesenchymal stem cells by subjecting a fetal appendage such as amniotic membrane to an enzyme treatment. The enzyme may include collagenase and/or metalloproteinase. As the metalloproteinase, thermolysin and/or dispase can be mentioned, but it is not particularly limited. The enzyme treatment may preferably be performed by combining collagenase and metalloproteinase. More preferably, the fetal appendages are simultaneously processed at once by combining the aforementioned enzyme. For the enzyme treatment of the fetal appendage, it is preferable to treat the amniotic membrane which has been washed with a washing solution such as physiological saline solution or Hank's balanced salt solution, by immersing the amniotic membrane in the enzyme solution and stirring with stirring means. As such stirring means, for example, a stirrer or a shaker can be used from the viewpoint of efficiently liberating the mesenchymal stem cells contained in the extracellular matrix layer of the fetal appendage, but it is not limited thereto. After the enzyme treatment, mesenchymal stem cells may be separated and purified by a known method such as a filter, centrifugation, hollow fiber separation membrane, cell sorter and the like. Preferably, mesenchymal stem cells are purified by the filter. The mesenchymal stem cells passed through the filter can be recovered by centrifugation after diluting the filtrate with double or more medium or a balanced salt buffer such as physiological saline, Dulbecco's phosphate buffer (DPBS), Earle's balanced salt solution (EBSS), Hanks balanced salt solution (HBSS), phosphate buffer (PBS) and the like.

Adipose tissue-derived MSCs may be used from purchasing commercially available adipose derived stem cells and from stromal vascular fraction (SVF) by collecting adipose tissue from a mammal and treating it with enzyme such as collagenase.

A method for culturing mesenchymal stem cells, for example, may include a step of seeding a cell population in an uncoated plastic culture vessel at a density of 100 to 20,000 cells/cm$^2$. The lower limit of the cell density is more preferably 200 cells/cm$^2$ or more, further preferably 400 cells/cm$^2$ or more, further preferably 1,000 cells/cm$^2$ or more. The upper limit of the cell density is more preferably 10,000 cells/cm$^2$ or less, further preferably 8,000 cells/cm$^2$ or less, further preferably 6,000 cells/cm$^2$ or less. In another embodiment of the culturing method, for example, cells are cultured by adding growth factor such as human platelet lysate (hPL), fetal bovine serum (FBS), basic fibroblast growth factor (bFGF), bovine platelet lysate, bovine platelet rich plasma derived serum, human platelet rich plasma derived serum, or other serum to a basal medium. The basal medium is not particularly limited, for example, BME medium, BGJb medium, CMRL 1066 medium, Glasgow MEM medium, improved MEM Zinc Option medium, IMDM medium (Iscove's Modified Dulbecco's Medium), Medium 199 medium, Eagle MEM medium, αMEM Minimum Essential Medium Eagle) medium, DMEM medium (Dulbecco's Modified Eagle's Medium), Ham's F10 medium, Ham's F12 medium, RPMI 1640 medium, Fischer's medium and a mixed medium thereof such as DMEM/F12 medium Dulbecco's Modified eagle's Medium/Nutrient Mixture F-12 Ham)) are preferably used.

The cultured cells can be further passaged and cultured, for example, cells are treated with a cell detaching agent from a plastic culture container. Then, the obtained cell suspension is centrifuged, the supernatant is removed, and the obtained cell pellet is resuspended in the medium. Finally, cells are seeded in plastic culture containers filled with a medium, and cultured in a CO2 incubator. An example of the cell detaching agent may be trypsin, collagenase, dispase, ethylenediaminetetraacetic acid (EDTA) and the like. A commercially available cell detaching agent may be preferably used such as trypsin-EDTA solution (manufactured by Thermo Fisher Scientific), TrypLE Select (manufactured by Thermo Fisher Scientific), Accutase (manufactured by Stemcell Technologies), Accumax (manufactured by Stemcell Technologies), and the like. According to the aforementioned cell culturing method of the present invention, a safe cell preparation (pharmaceutical composition) can be provided.

The cell culturing method of the present invention may include a step of cryopreservation of the cells. In the embodiment of the cryopreservation step, cells may be separated, collected, cultured, used or mixed to the multilayer matrix after thawing the cells. When cryopreserved, the cells may be frozen in any storage container. Examples of such storage containers include, but are not limited to, cryotubes, cryovials, freezing bags, infusion bags, and the like. The cells may be cryopreserved in any cryopreservation solution exemplified in the embodiment of "the cell suspension applied to the second layer".

The method for producing a multilayer matrix may include a step of preparing a cell suspension. The cell suspension is composed of both cells and a solution. The solution may include saline, phosphate buffered saline, Ringer's solution containing bivalent cation (for example, calcium chloride or magnesium chloride), or a medium. The medium may include HBSS(+), HBSS(−), RPMI, IMEM, DMEM, MEM, and/or cell preservatives, which may be optionally supplemented with serum, plasma, protein-containing solution. A commercially available cryopreservation solution may be preferably used as the solution. For example, CP-1 (manufactured by Kyokuto Pharmaceutical Industry Co., Ltd.), BAMBANKER (manufactured by Lymphotec Corporation), STEM-CELLBANKER (manufactured by Nippon Zenyaku Kogyo Co., Ltd.), ReproCryo RM (manufactured by ReproCell), CryoNovo (Akron Biotechnology, MSC Freezing Solution (manufactured by Biological Industries), CryoStor (manufactured by HemaCare), and the like. The cell preservatives may be a solution of a combination of one or two or more of the above-listed solutions with one or two or more of cryopreservative such as dimethyl sulfoxide, albumin, glycerol, hydroxyethyl starch, or dextran. The concentration of dimethyl sulfoxide is preferably 3 wt % or more, 4 wt % or more, 5 wt % or more. The upper limit of the concentration of dimethyl sulfoxide is 10 wt % or less, 9 wt % or less, 8 wt % or less, 7 wt % or less. The concentration of albumin is preferably 0.5 wt % or more, 1 wt % or more, 2 wt % or more, 3 wt % or more. The upper limit of the concentration of albumin is 8 wt % or less, 7 wt % or less, 6 wt % or less, 5 wt % or less. The concentration of hydroxyethyl starch is preferably 3 wt % or more, 4 wt % or more, 5 wt % or more. The upper limit of the concentration of hydroxyethyl starch is 9 wt % or less, 8 wt % or less, 7 wt % or less. One example of cell preservatives includes a composition of 5 wt % of dimethyl sulfoxide, 6 wt % of hydroxyethyl starch, and 4 wt % of human serum albumin.

In an embodiment of the step of preparing a cell suspension, cultured cells are treated with a cell detaching agent from a plastic culture container at first. Then the obtained cell suspension is centrifuged, the supernatant is removed, and the obtained cell pellet is resuspended in the solution to be the cell suspension. The cell suspension may be applied to the second layer of the multilayer matrix directly or via cryopreservation. The concentration of the cell suspension may be $5 \times 10^6$ cells/mL or more, $6 \times 10^6$ cells/mL or more, $8 \times 10^6$ cells/mL or more, $10 \times 10^6$ cells/mL or more, $20 \times 10^6$ cells/mL or more, $40 \times 10^6$ cells/mL or more, $60 \times 10^6$ cells/mL or more. There are no upper limits of cell concentration of the cell suspension, because great therapeutic effect can be achieved as the cell concentration is increased. However, it is preferable that the concentration of the cell suspension is $133 \times 10^6$ cells/mL or less, $100 \times 10^6$ cells/mL or less. For example, from $10 \times 10^6$ cells/mL to $80 \times 10^6$ cells/mL are preferably used. When the number of the cells is less than $5 \times 10^6$ cells/mL, the number of the cells added to the multilayer matrix is too small, and the therapeutic effect may not be achieved. When the number of the cells exceeds $133 \times 10^6$ cells/mL, the cells become a pellet so that preparation of a cell suspension becomes physically difficult.

The method for producing a multilayer matrix may include a step of applying the cell suspension to the second layer of the multilayer matrix. In an embodiment of the step of applying the cell suspension to the second layer, the cell suspension may be taken into syringe with a blunt needle and flatly applied on the bioadhesive layer. The volume of cell suspension added may be of from 20 µL/cm² or more, 22 µL/cm² or more, 24 µL/cm² or more. The upper limit of the volume of cell suspension is 60 µL/cm² or less, 55 µL/cm² or less, 50 µL/cm² or less. When the volume is less than 20 µL/cm², the fibrinogen/thrombin side does not get wet enough, poor formation of adhesive fibrin may occur and adhesive ability to a tissue or an organ may decrease. When the volume exceeds 60 µL/cm², the amount of suspension becomes too large so that a part of the suspension may drip from the bioadhesive layer and the whole amount of the cells cannot be applied to the multilayer matrix.

The cells, which are positive to CD105, CD73 and CD90 and are negative to CD45 and CD34 in the present invention, are generally defined as mesenchymal stem cells. The percentage of the aforementioned cells exhibiting positive to CD105, CD73 and CD90 is 50% or more. The percentage is preferably 60% or more, more preferably 70% or more, and further preferably 90% or more. The percentage of the aforementioned mesenchymal stem cells exhibiting positive to CD45 and CD34 is 10% or less, preferably 5% or less, and more preferably 3% or less.

The cells exhibiting positive to CD142 are preferably used in the present invention as the CD142 positive cells secrete tissue factors which relate coagulation or cell adhesion so that high engraftment (retention) rates of cells can be achieved. The percentage of the aforementioned cells exhibiting positive to CD142, which are used in the present invention, is 50% or more. The percentage is preferably 60% or more, more preferably 70% or more, and further preferably 90% or more. The percentage of the aforementioned cells exhibiting positive to CD106, which are used in the present invention, is 10% or less. The percentage is preferably 5% or less, and more preferably 3% or less. The expression markers (CD73, CD90, CD105, CD34, CD45, CD142, and CD106) can be detected by any given detection methods, which have been known in the present technical field. Examples of the method of detecting the expression markers include flow cytometry and cell staining, but are not limited to. In the flow cytometry using a fluorescence-labelled antibody, when cells emitting a stronger fluorescence than a negative control (isotype control) are detected, the cells are determined to be "positive" to the concerned marker. Any given antibody that is known in the present technical field can be used as a fluorescence-labelled antibody. Examples of such a fluorescence-labelled antibody include antibodies labelled with fluorescein isothiocyanate (FITC), phycoerythrin (PE), allophycocyanin (APC), etc., but are not limited to. In the cell staining, when cells that are colored or emit fluorescence are observed under a microscope, the cells are determined to be "positive" to the concerned marker. The cell staining may be either immunological cell staining in which antibodies are used, or non-immunological cell staining in which antibodies are not used.

The timing of detecting aforementioned surface antigens is not particularly limited, but for example, during cell culture, before cryopreservation, after thawing, before preparing a pharmaceutical composition, before mixing it to multilayer matrix or before administration to patients.

The term "kit" refers to a kit product which is composed of a multilayer matrix packed in a container as a sealed dosage form and a cell suspension packed in a container. In one embodiment of the kit, the multilayer matrix and the cell suspension may be provided separately but used together. In another embodiment of the kit, the multilayer matrix and the cell suspension may be provided at the same time and used together. The cell suspension and multilayer matrix are combined prior to use, for example, the cell suspension is applied in and/or on to the multilayer matrix before administration. The kit may be a pharmaceutical composition. According to the present invention, a pharmaceutical composition comprising a cell population comprising mesenchymal stem cells, a pharmaceutically acceptable medium and a pharmaceutically acceptable multilayer matrix may be provided in the present invention. The pharmaceutical composition of the present invention may be a cell population comprising mesenchymal stem cells diluted with a pharmaceutically acceptable medium. The above-mentioned pharmaceutically acceptable medium is not particularly limited as long as it is a solution that can be administered to a patient or a subject. The pharmaceutically acceptable medium may be an infusion, for example, water for injection, physiological saline, 5% dextrose, Ringer's solution, Ringer's lactate solution, Ringer's acetate solution, bicarbonate Ringer's solution, amino acid solution, starting solution dehydrated replenisher (No. 2 solution), maintenance infusion solution (No. 3 solution), postoperative recovery solution (No. 4 solution), Plasma-Lyle A. A package of the pharmaceutical composition may be cryotubes, cryovials, freezing bags, infusion bags, and the like.

The lesion or trauma may be heart disease, spinal cord injury or an ulcer. The lesion or trauma may be the result of a disease process or the result of surgery as part of a surgical procedure. The term "Organ" refers to a group of tissues which perform a specific function or group of functions. The organ may be heart, liver, kidney, lung, spleen, or pancreas. The term "Tissue" refers to an aggregate of cells in an organism which have similar structure and functions. The tissue may be skin, skeletal muscle or nervous tissue, for example spinal cord, brain or a nerve ganglion. The tissue may be an element of the gastro-intestinal (GI) tract, for example, the oesophagus, stomach, intestines and rectum/anus. The heart disease may comprise acute myocardial infarction (AMI), ischaemic cardiomyopathy, dilated cardiomyopathy, hypertrophic cardiomyopathy, myocarditis and other types of acute and chronic heart failure.

The methods of the present invention may be applied to heart disease patients undergoing cardiac surgery such as coronary artery bypass grafting (CABG), left ventricular assist device implantation, valve repair/replacement and correction surgery for congenital diseases. The number of these patients is not small, and the incidence of such heart diseases is likely to soar along with the increase of old populations. It is known that addition of cell therapy enhances the outcome of CABG (Donndorf et al., Intramyocardial bone marrow stem cell transplantation during coronary artery bypass surgery: A meta-analysis, *J Thoracic Cardiovasc Surg* 2011; 142(4), 911-920). Increased blood flow via the bypass and increased angiogenesis by cell therapy will synergistically enhance myocardial perfusion. In turn, improved perfusion by CABG will help donor cell survival and improve the effect of cell therapy.

The methods of the present invention may also be solely applied to heart disease patients via thoracotomy or by using endoscopy, thoracoscopy or mediastinoscopy. The methods may also be applied in combination with percutaneous coronary intervention.

The invention therefore also extends to a method of treating a patient suffering from a lesion or trauma to a tissue or an organ, for example a myocardial infarction, comprising applying a multilayer matrix to the surface of the tissue or organ wherein said multilayer matrix comprises at least two layers in which the first layer comprises a bioresorbable material and the second layer comprises a bioadhesive material and wherein prior to applying the multilayer matrix a cell suspension is applied to the second layer. Suitably, the multilayer matrix is applied to the epicardium of the heart. The invention therefore provides a method for epicardial placement of cells (or "cell-dressing"), for example stem cells.

The addition of the cell suspension and/or drugs to the second layer provides a source of moisture sufficient to activate the bioadhesive material, for example fibrinogen and thrombin to produce a fibrin glue. The fibrin glue can keep cells and/or drugs on the surface of an organ or tissue, which results in higher engraftment (retention) rate of cells and/or drugs than the previous transplantation methods such as intramyocardial injection and cell sheets.

In accordance with the invention, there is therefore provided a combination of a multilayer matrix as described above and a cell suspension for separate sequential, stepwise or simultaneous administration in the treatment of a lesion or trauma to a tissue or an organ, for example myocardial infarction.

The method of treatment may be carried out during a surgical procedure to repair the damaged organ, for example CABG. The invention therefore includes use of the cell-coated multilayer matrix in a method of surgery to treat a patient suffering from a heart disease, including myocardial infarction and cardiomyopathy.

There is therefore provided a kit of parts comprising a multilayer matrix as described above and a cell suspension and/or drugs.

There is therefore provided a process for the preparation of a cell-coated multilayer matrix comprising at least two layers in which the first layer comprises a bioresorbable material and the second layer comprises a bioadhesive material, and comprising applying a cell suspension to the second layer of the multilayer matrix.

In one embodiment of the invention, the multilayer matrix may comprise two layers in which the first layer comprises a bioresorbable material and the second layer comprises a bioadhesive material, in which the bioresorbable material is equine collagen formulated with the following excipients: human albumin, riboflavine, sodium chloride, sodium citrate, and L-arginine hydrochloride. The bioadhesive material is human fibrinogen and human thrombin.

Suitably, the bioadhesive material is prepared as a dried coating on the bioresorbable material in which the human fibrinogen is present at from 2.0 mg to 10.0 mg per $cm^2$, for example 5.5 mg per $cm^2$ and the human thrombin is present at from 0.5 IU to 5.0 IU per $cm^2$, for example 2.0 IU per $cm^2$.

The cells may be added to the bioadhesive layer at a density of $0.3 \times 10^6$ or more per $cm^2$ of multilayer matrix, more preferably $0.5 \times 10^6$ per $cm^2$ or more, further preferably $1 \times 10^6$ or more per $cm^2$. There are no upper limits of cell density added to the bioadhesive layer, because great therapeutic effect can be achieved as the cell density getting large. However, it is preferable that cells may be added at a density of $4.2 \times 10^6$ per $cm^2$ or less of multilayer matrix, more preferably $4.1 \times 10^6$ per $cm^2$ or less, further preferably $4.0 \times 10^6$ per $cm^2$ or less. For example, $0.5 \times 10^6$ per $cm^2$ or $4.0 \times 10^6$ per $cm^2$ is preferably used. When the density is less than $0.3 \times 10^6$ per $cm^2$, the number of the cells added is too small and therapeutic effect cannot be achieved. In the present invention, the density of cells added to the bioadhesive layer can be set in the favorable range depending on the weight and severity of the patient. Also, in the present invention, higher density of cells can be administrated than conventional cell sheets.

It may be physically difficult to apply the cells at a density of more than $4 \times 10^6$ cells/$cm^2$ to multilayer matrix, since the cells become a pellet or the amount of suspension becomes too large so that the cells cannot be applied to multilayer matrix. The volume of cell suspension added may be of from 20 µL/$cm^2$ to 60 µL/$cm^2$ for example. When the volume is less than 20 µL/$cm^2$, the fibrinogen/thrombin side does not get wet enough, poor formation of fibrin may occur and adhesive ability to a tissue or an organ may decrease. When the volume exceeds 60 µL/$cm^2$, the amount of suspension becomes too large so that a part of the suspension may be dripped from the bioadhesive layer and whole amount of the cells cannot be applied to multilayer matrix. In the present invention, the volume of cell suspension added to the bioadhesive layer can be set in the favorable range depending on the weight and severity of the patient. Also, in the present invention, higher density of cells can be administrated by adding high volume of cell suspension the bioadhesive layer than conventional cell sheets.

The cells added to the bioadhesive layer may be added at a concentration of $5 \times 10^6$ cells/mL to $133 \times 10^6$ cells/mL, more preferably $10 \times 10^6$ cells/mL to $80 \times 10^6$ cells/mL. When the number of cells is less than $5 \times 10^6$ cells/mL, the number of cells added is too small, and the therapeutic effect may not be achieved. When the number of cells exceeds $133 \times 10^6$ cells/mL, the cells become a pellet so that preparation of cell suspension becomes physically difficult. In the present invention, the cell concentration added to the bioadhesive layer can be set in the favorable range depending on the weight and severity of the patient. Also, in the present invention, a higher density of cells can be administrated by adding high concentration of cell suspension to the bioadhesive layer than conventional cell sheets.

The multilayer matrix may be prepared as a sealed dosage form ready for use. The sealed dosage form may be supplied in a blister pack in order to preserve the contents. Suitable pack sizes are (1.0 to 10 cm)×(1.0 to 10 cm), for example 9.5 cm×4.8 cm, 4.8 cm×4.8 cm, 3.0 cm×2.5 cm, 2.5 cm×2.5 cm, or 1.0 cm×1.0 cm. The packs may contain one or more matrices. Alternatively, the matrix may be cut to size during the surgical procedure.

Upon administration of a multilayer matrix to a mammal, the administrating area of the multilayer matrix per body weight is preferably 0.1 $cm^2$/kg or more. It is more preferably 1 $cm^2$/kg or more, and further preferably 2 $cm^2$/kg or more. The administrating area of the multilayer matrix per body weight is preferably 6 $cm^2$/kg or less. It is more preferably 5 $cm^2$/kg or less. If the administrating area of the multilayer matrix is less than 0.1 $cm^2$/kg, it is likely that the therapeutic effects cannot be obtained because the number of cells administered is too small. There are no upper limits of the area of the multilayer matrix, because great therapeutic effect can be achieved as the area gets large. However, the therapeutic effect may be saturated if the administrating area of the multilayer matrix exceeds 6 $cm^2$/kg.

Upon administration of a multilayer matrix to a human whose body weight is 40-100 kg and 2 $cm^2$/kg of the multilayer matrix is applied to the human, for example, the area of the multilayer matrix administrating to the human is 80-200 $cm^2$. Upon administration of a multilayer matrix to a pig whose body weight is 15-30 kg and 3 $cm^2$/kg of the multilayer matrix is applied to the pig, for example, the area of the multilayer matrix administrating to the pig is 45-90 $cm^2$. Upon administration of a multilayer matrix to a rat whose body weight is 150-300 g and 5 cm$^2$/kg of the multilayer matrix is applied to the rat, for example, the area of the multilayer matrix administrating to the rat is 0.75-1.5 cm$^2$.

The methods of the invention have multiple important advantages in the feasibility and efficiency for stem/progenitor cell therapy for heart failure, over other methods as follows:

(1) Advantage over current injection methods (intramyocardial, intracoronary and intravenous injection):
  (i) Compared to any current injection methods, the method of the present invention achieves significantly greater initial retention and increased presence of donor cells in the heart because the fibrin glue can keep cells on the surface of the heart. This will result in the augmentation of the therapeutic effect of cell therapy for the treatment of heart failure.
  (ii) Intramyocardial cell injection results in formation of clusters of donor cells within the heart, which involves inflammation. Such heterogeneity within the myocardium can be a source of arrhythmia occurrence. This adverse change does not occur by the method of the present invention.
  (iii) Intracoronary injection has a risk of coronary embolism. This is particularly critical when larger cell types, such as MSCs, are injected into diseased, narrowed coronary arteries. Intravenous injection carries a risk of pulmonary embolism. While in contrast, the method of the present invention does not have such a risk at all.
  (iv) Intravenous injection (as well as intracoronary and intramyocardial injection) causes ectopic delivery of donor cells into unwanted organs, for example the lung, which may cause adverse effects. The method of the present invention has a much less risk of such a complication (as most of donor cells are retained on the heart surface).

(2) Advantage over other epicardial placement methods
  (i) The use of any tissue engineering constructs, including the cell sheet technique and biological constructs (such as collagen sponge) incorporating stem cells, requires a prolonged time to produce in a high-grade cell processing facility. In contrast, the method is produced from a cell suspension and a suitable substrate matrix material as described herein in a usual surgical theatre or other treatment room, when donor cells are provided externally. No specific cell processing facility is necessarily required in each hospital.
  (ii) Quality control/assurance of tissue engineering constructs, including the cell sheets and tissue-engineered constructs incorporating stem cells, is very demanding. Storage and transport/delivery of these products are also challenging. This concern is obviated in the methods of the present invention therapy because the donor cells are added to the biocompatible patch immediately before placement to the heart without storage. The methods to transport/store stem cells have been established. There is no need of transport/delivery of the fragile final biological products (final cell-multilayer matrix complex).
  (iii) Tissue engineering constructs including cell sheets cannot be produced with non-adherence floating cells. For example, unfractionated bone marrow mononuclear cells (BMMNC) are the most frequently used donor cell type in clinical studies, but these are mostly floating cells and cannot form a cell sheet. In contrast, the method of the present invention is applicable with both adherent and non-adherent cells.
  (iv) Cell sheets are quite fragile, requiring extreme caution and specialist expertise, whilst the multilayer matrix of the present invention is sufficiently firm and easy to handle.
  (v) The tissue engineering constructs, including biological constructs incorporating stem cells, requires sutures to fix onto the heart surface, which could damage the heart or coronary vessels. While in the present invention, such a risky procedure is not needed.
  (vi) Cell sheets cannot freely set the cell density. While in the present invention, the cell density can be set in the favorable range depending on the weight and severity of the patient by adjusting the cell concentration and the volume of cell suspension on and/or in the multilayer matrix. Also, in the present invention, higher doses of cells can be administrated than cell sheets.

The methods of the present invention are simple and straightforward and can be conducted by any ordinary clinician/hospital staff without extensive expertise or specific equipment like cell processing centre. The whole process of production of the cell-dressing completes only in 10 minutes in the surgical/treatment room. Immediately, this product may be simply applied to the patient. Thus, the methods of the present invention can be readily added during the course of surgery when required.

A commercially available bioresorbable material-supported fibrin patch (TachoSil®, EVARREST®) can be preferably used because it is already widely used in clinical practice for the purpose of haemostasis during surgery including cardiac operations. This material, whose safety has been proven and GMP-grade production facility has been established, can be directly used in the methods of the present invention as a convenient source material.

Preferred features of the second and subsequent aspects of the invention are as for the first aspect mutatis mutandis.

The invention will now be further described by way of reference to the following examples and drawings which are presented for the purposes of illustration only. In the examples, reference is made to a number of figures in which FIG. 1 shows the procedure for cell transplantation using Seprafilm® (a single layer material).

FIG. 2 shows unsuccessful results of cell transplantation using Seprafilm® (a single layer material) using 10×10$^6$ rat bone marrow mononuclear cells (BMMNCs). BMMNC-Seprafilm® complex was transplanted onto the rat heart surface at 28 days after myocardial infarction (SF-BMMNC group). Control group received sham operation at 28 days after myocardial infarction. Cardiac function was measured by echocardiography at Day 28 after treatment.

FIG. 3 shows unsuccessful results of cell transplantation using Seprafilm® and mesenchymal stem cells. 4×10$^6$ rat bone marrow-derived mesenchymal stem cells (MSCs) were transplanted onto the rat heart surface with aid of Seprafilm® at 28 days after myocardial infarction (SF-MSC group). Control group received sham operation at 28 days after myocardial infarction. Cardiac function was measured by echocardiography at Day 28 after treatment.

FIG. 4 shows donor cell leakage after Seprafilm® (SF)-aided cell delivery. A certain number of donor cells (labelled with red fluorescent dye, CM-Dil) retained on the heart surface after SF-aided cell delivery (FIGS. 4(a) & 4(b)). Following epicardial placement of Dil (pink)-labelled BMMNCs (FIG. 4(c)) with aid of Seprafilm®, cells were collected from the pericardial fluid. Many donor BMMNCs were found leaked (dropped off) in the pericardial cavity (yellow arrows).

Figure 7:
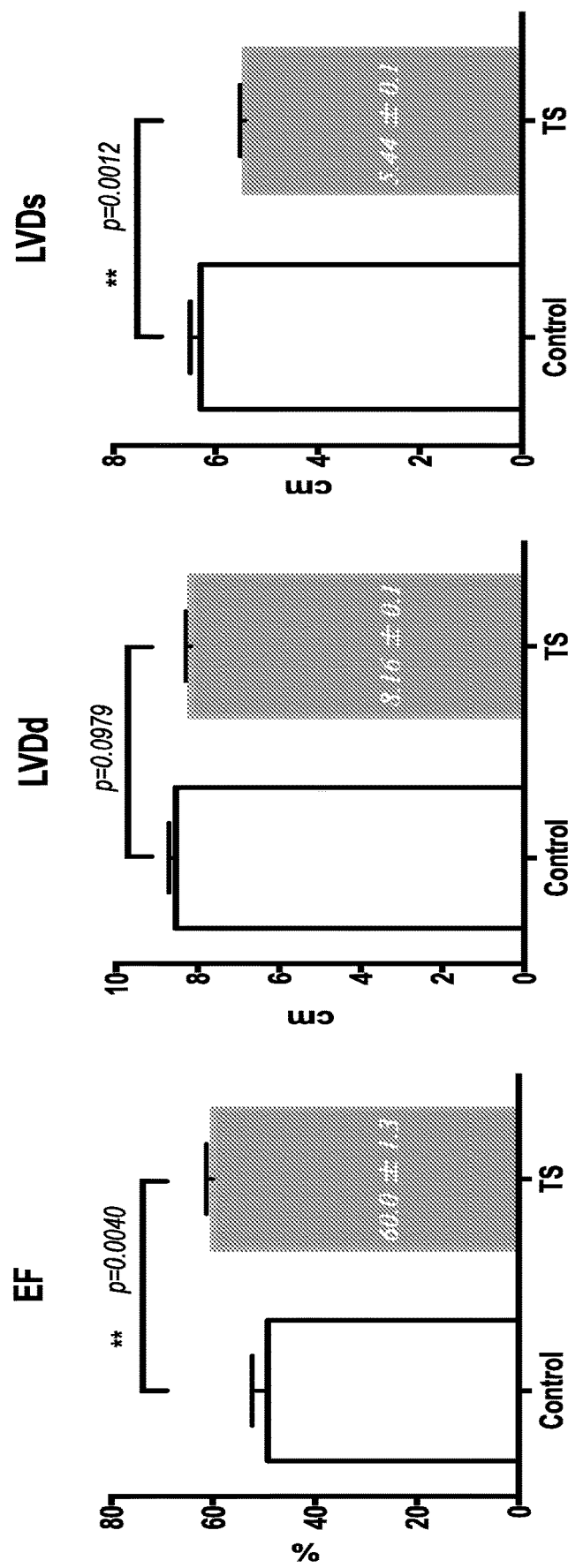

FIG. 7 shows therapeutic efficacy of epicardial placement of TachoSil®-mesenchymal stem cells (MSC) at Day 28 in a rat acute myocardial infarction model. 1×10$^6$ rat fetal membrane-derived MSCs were transplanted onto the rat heart surface with aid of TachoSil® at 1 hour after myocardial infarction (TS group). Control group received sham operation at 1 hour after myocardial infarction. Cardiac function was measured by echocardiography at Day 28 after treatment.

Figure 8:
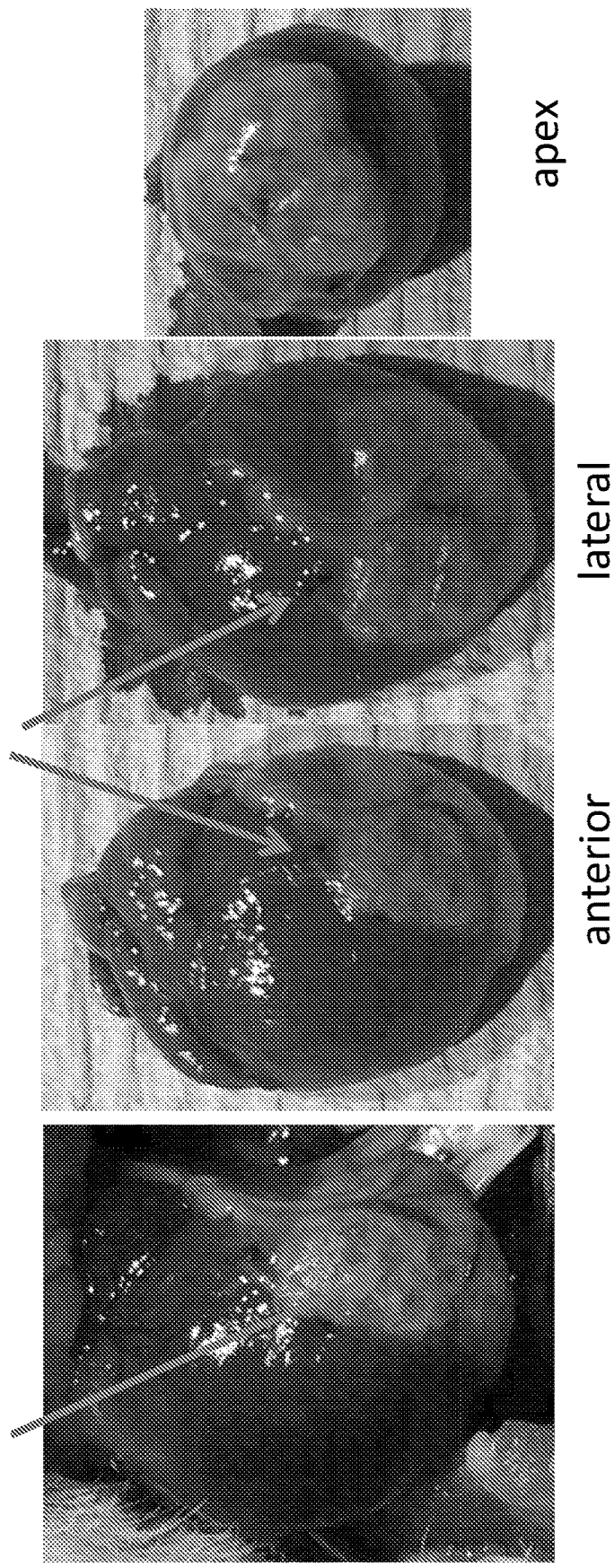

FIG. 8 shows the macroscopic observation at Day 5 after TachoSil®-MSC therapy in a rat acute myocardial infarction model. At Day 5 after epicardial placement of 1×10$^6$ rat fetal membrane-derived MSCs with aid of TachoSil®, TachoSil®-MSC complex was found to be firmly adhered to the heart surface.

Figure 9:
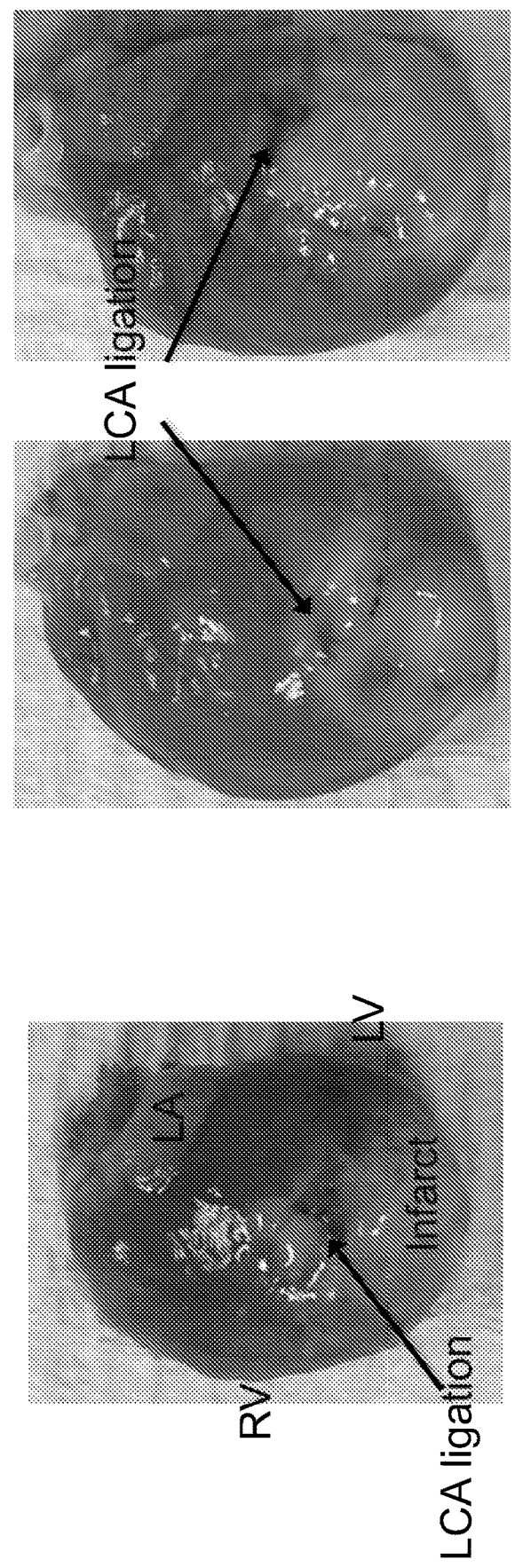

FIG. 9 shows the macroscopic observation at Day 28 after TachoSil®-MSC therapy in a rat acute myocardial infarction model. At Day 28 after epicardial placement of 1×10$^6$ rat fetal membrane MSCs with aid of TachoSil®, TachoSil®-MSC complex had mostly disappeared. There was no adverse change (complication) found.

Figure 10:
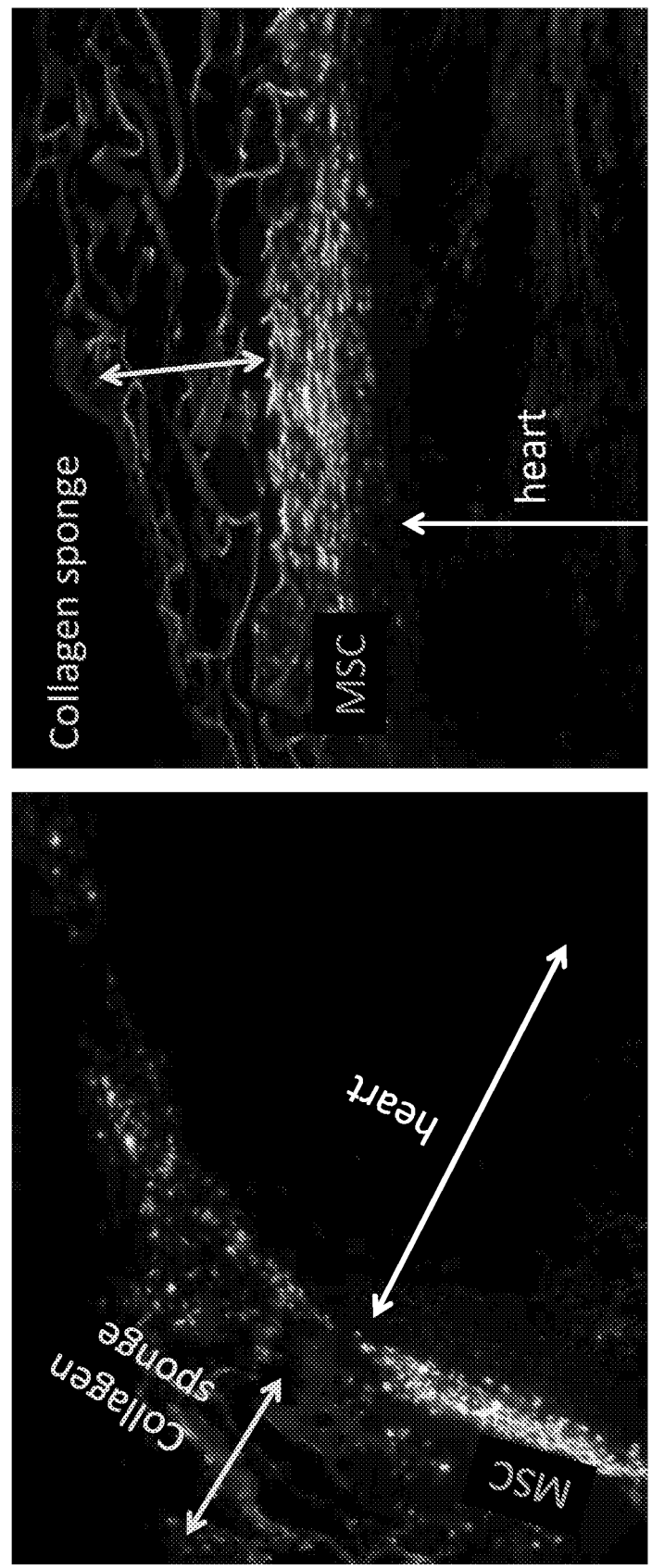

FIG. 10 shows donor cell survival at Day 5 after TachoSil®-MSC transplantation on the rat heart. At Day 5 after epicardial placement of 1×10$^6$ rat fetal membrane-derived MSCs with aid of TachoSil®, a large number of donor MSCs (orange) were observed on the surface of the heart. There was little migration of MSCs into the myocardium, whilst some MSCs settled in the collagen sponge layer.

Figure 11:
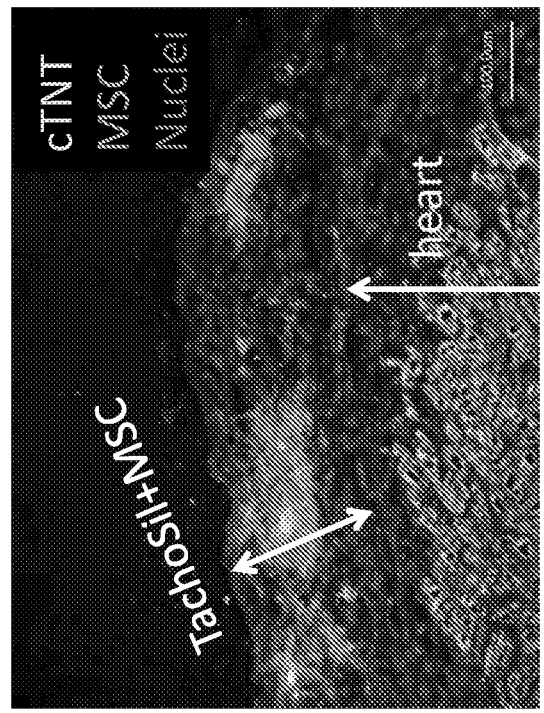
Figure 11:
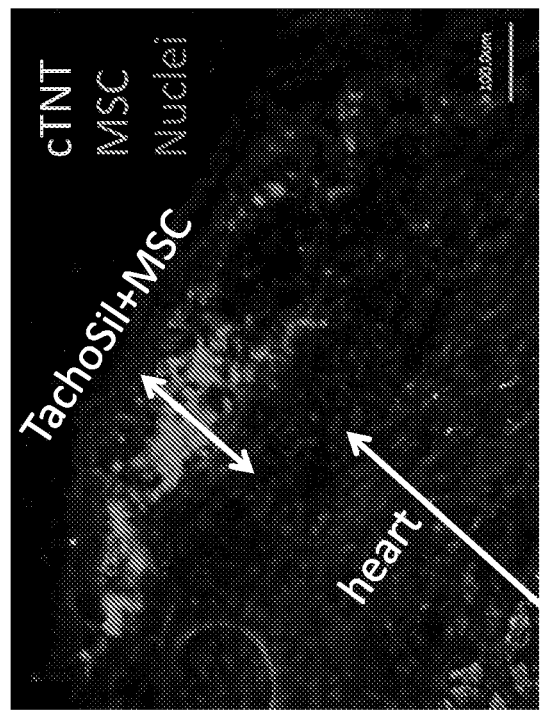

FIG. 11 shows donor cell survival at Day 28 after TachoSil®-MSC transplantation on the rat heart. At Day 28 after epicardial placement of 1×10$^6$ rat fetal membrane-derived MSCs with aid of TachoSil®, a number of donor MSCs (orange) were observed on the surface of the heart. There was little migration of MSCs into the myocardium. Collagen of TachoSil® appeared to be absorbed or disappeared.

Figure 12:
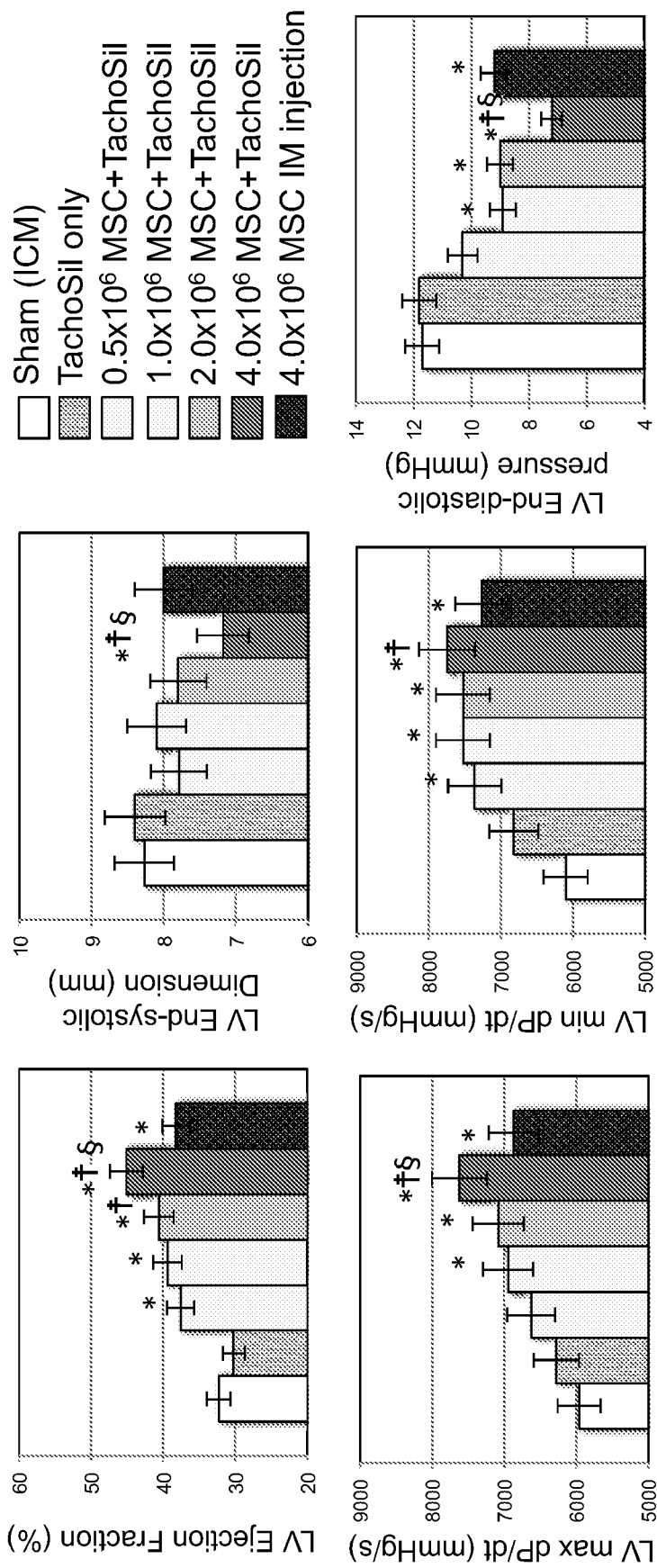

FIG. 12 shows therapeutic efficacy of epicardial placement of TachoSil®-MSC at Day 28 in a rat post myocardial infarction ischaemic heart failure model. Four weeks after left coronary artery ligation in rat (ischaemic heart failure model), TachoSil® seeded with a range of rat fetal membrane-derived MSCs, TachoSil only (TS only group), or nothing (Sham group) was placed on the heart surface. Cardiac function was measured by echocardiography (upper lanes) and catheterisation (lower lanes) at Day 28 after treatment.

Figure 13:
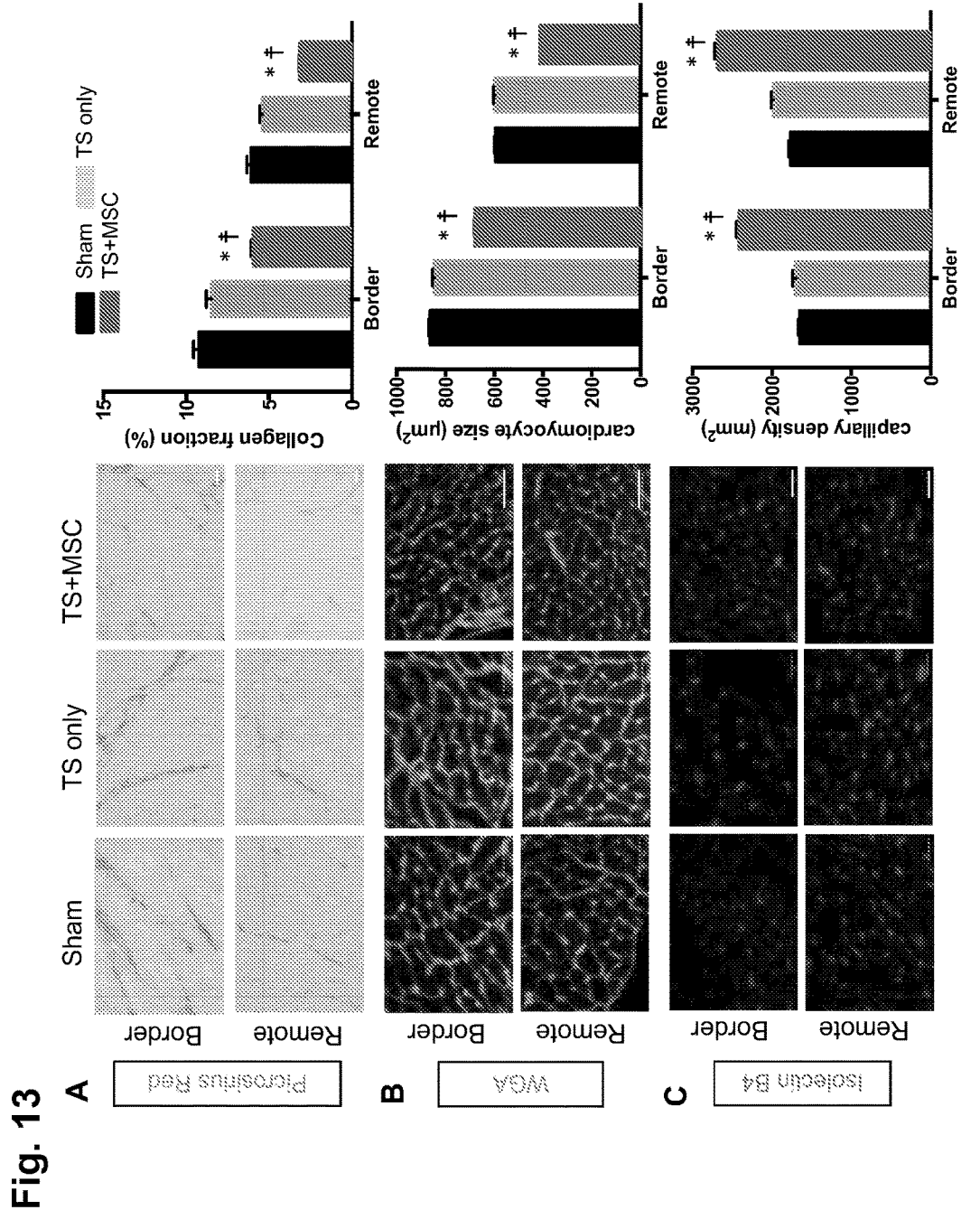

FIG. 13 shows improved repair of the damaged myocardium by epicardial placement of TachoSil®-MSC in a rat post myocardial infarction ischaemic heart failure model. Four weeks after left coronary artery ligation in rat, TachoSil® seeded with 4×10$^6$ rat fetal membrane-derived MSCs (TS+MSC group), TachoSil® only (TS only group), or nothing (Sham group) was placed on the heart surface. Four weeks after treatment, TS+MSC group showed significantly attenuated pathological fibrosis (A), reduced cardiomyocyte hypertrophy (B; WGA=Wheat germ agglutinin), and improved microvascular formation (C) in both remote and border areas of myocardial infarction, compared to both Sham and TS only groups. Scale bars; 10, 50, 30 mm in A, B, C, respectively.

Figure 14:
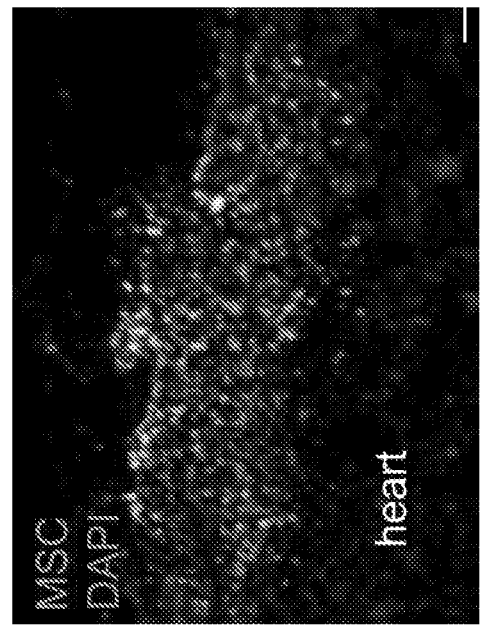
Figure 14:
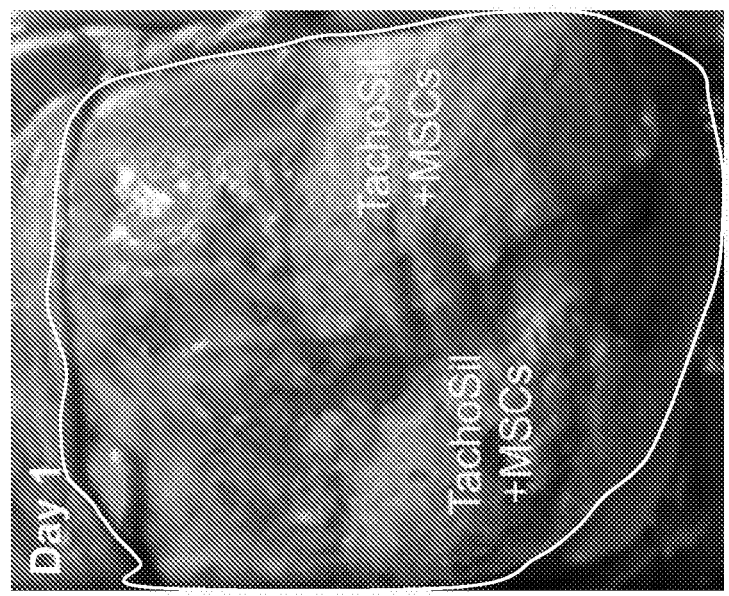

FIG. 14 shows feasibility of epicardial placement of TachoSil®-MSC on the pig heart. Two pieces of TachoSil® (25 cm$^2$) mixed with 1 mL of 5×10$^7$ cells/mL pig bone marrow-derived MSCs were placed on to the surface of the beating heart of pigs (20-22 kg). In addition to the technical feasibility, great retention and survival of MSCs (labelled orange with CM-Dil) was histologically confirmed at Day 1. Scale bar=100 μm.

Figure 15:
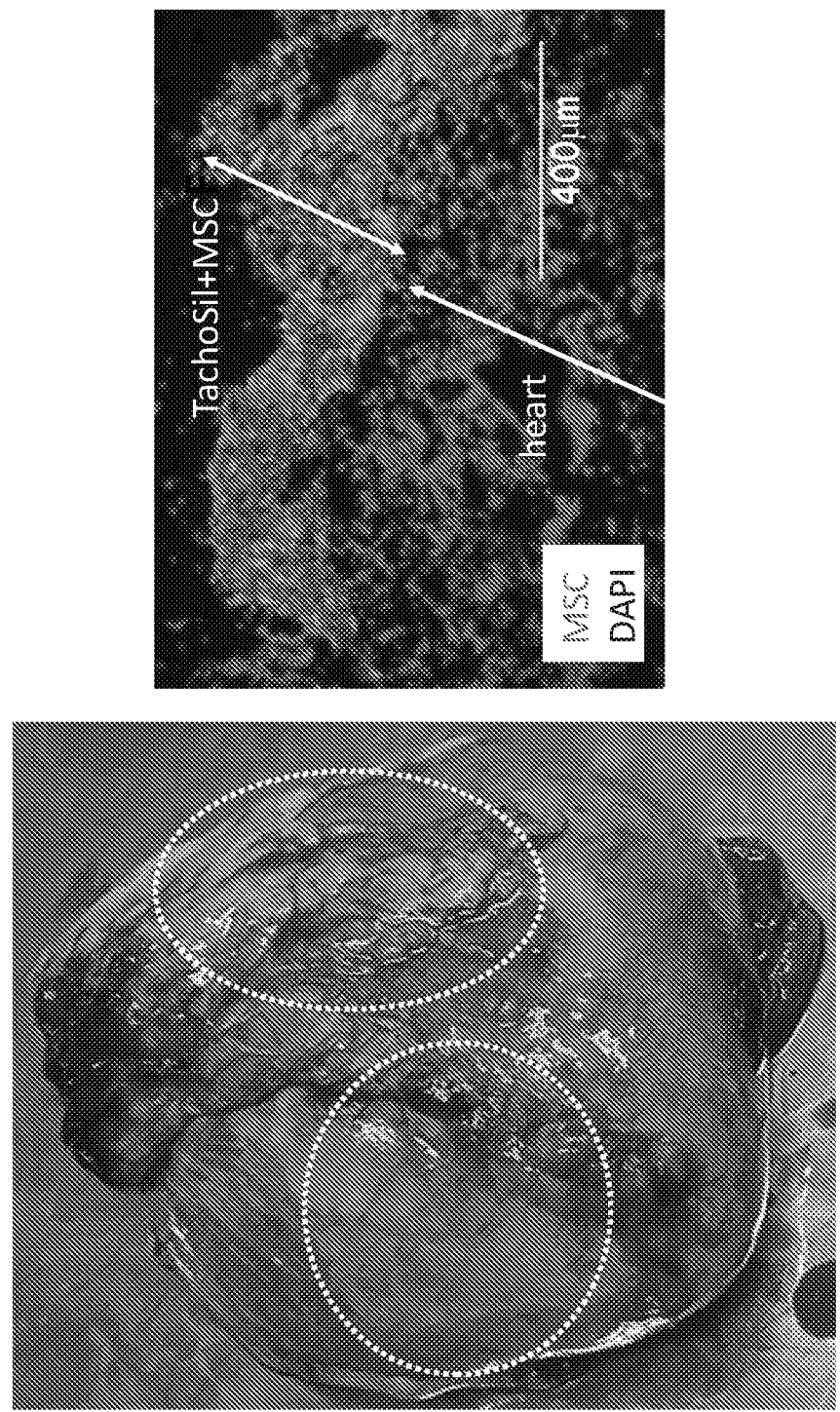

FIG. 15 shows feasibility of epicardial placement of TachoSil®-MSC on the pig heart. Two pieces of TachoSil® (25 cm$^2$) mixed with 1 mL of 8×10$^7$ cells/mL human amnion-derived MSCs were placed on to the surface of the beating heart of pigs (20-22 kg). In addition to the technical feasibility, great retention and survival of MSCs (labelled orange with CM-Dil) was histologically confirmed at Day 1. Scale bar=400 μm.

Figure 16:
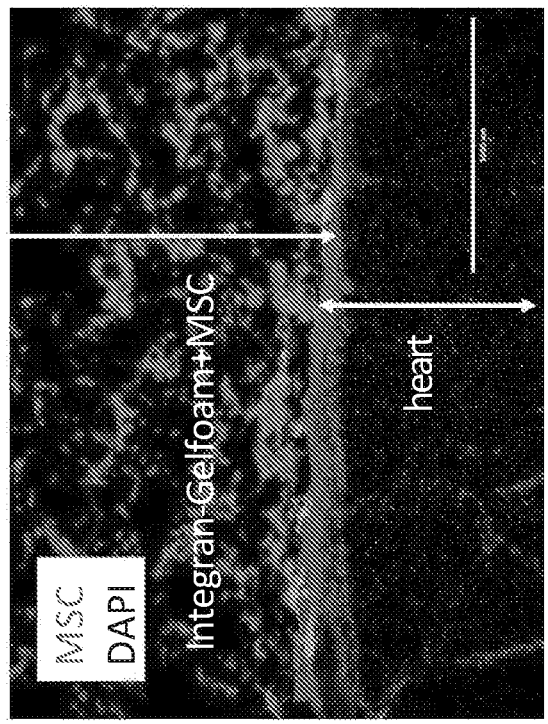

FIG. 16 shows feasibility of epicardial placement of Integran®-Gelfoam®-MSC on the pig heart. Integran®-Gelfoam® (9 cm$^2$) mixed with 1 mL of 8×10$^7$ cells/mL human amnion-derived MSCs were placed on to the surface of the beating heart of pigs (20-22 kg). In addition to the technical feasibility, great retention and survival of MSCs (labelled orange with CM-Dil) was histologically confirmed at Day 1. Scale bar=400 μm.

Figure 17:
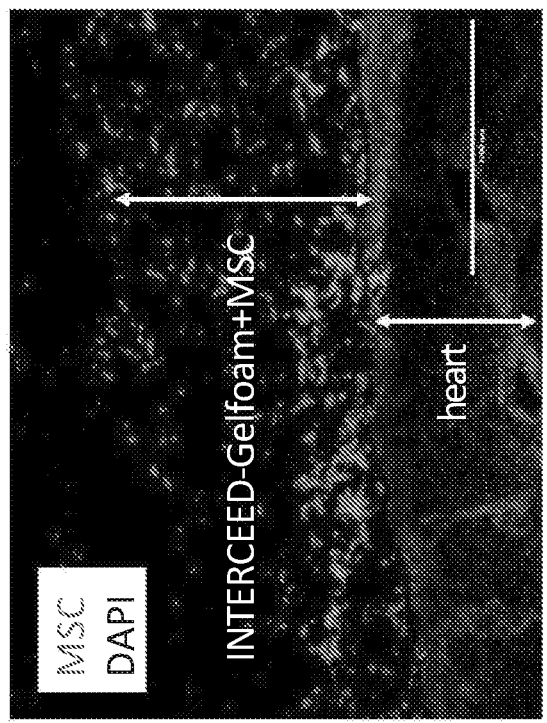

FIG. 17 shows feasibility of epicardial placement of INTERCEED®-Gelfoam®-MSC on the pig heart. INTERCEED®-Gelfoam® (9 cm$^2$) mixed with 1 mL of 8×10$^7$ cells/mL human amnion-derived MSCs were placed on to the surface of the beating heart of pigs (20-22 kg). In addition to the technical feasibility, great retention and survival of MSCs (labelled orange with CM-Dil) was histologically confirmed at Day 1. Scale bar=400 μm.

EXAMPLE 1: UNSUCCESSFUL TRIAL OF EPICARDIAL CELL PLACEMENT USING A MONOLAYER MATRIX (SEPRAFILM®)

Figure 1:
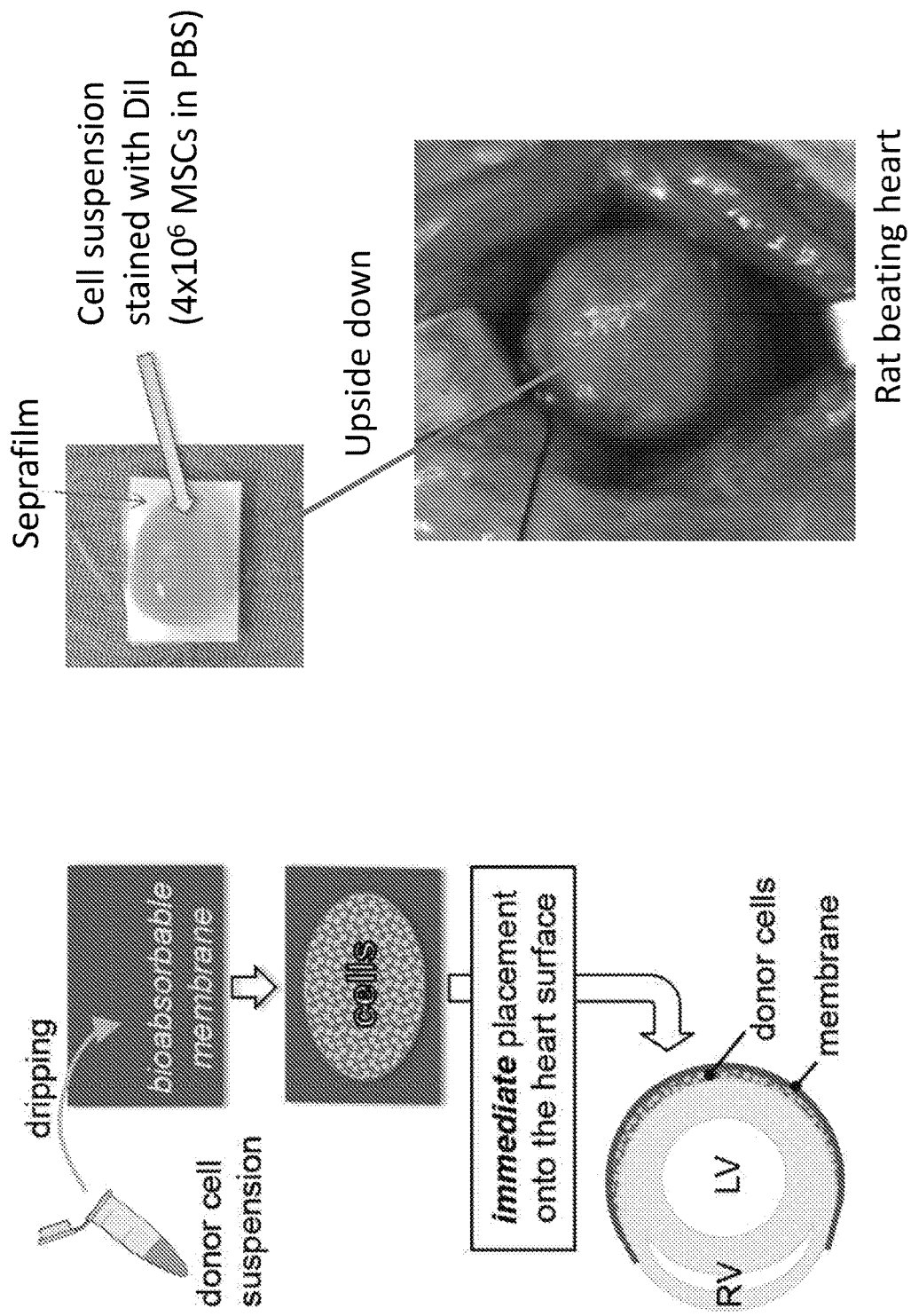

Epicardial placement of stem cells was first tried using a monolayer matrix. A most-widely used clinically-approved matrix, Seprafilm® (Sanofi) which is clinically used for prevention of post-surgical adhesion, was tested. Rat bone marrow mononuclear cells (10×10$^6$) or bone marrow-derived mesenchymal stem cells (MSCs; 4×10$^6$) were dissolved in 30 μL of HBSS and placed onto the 1 cm$^2$ Seprafilm®, which was turned upside down and directly placed onto the surface of the rat heart at 28 days after myocardial infarction (FIG. 1).

Figure 2:
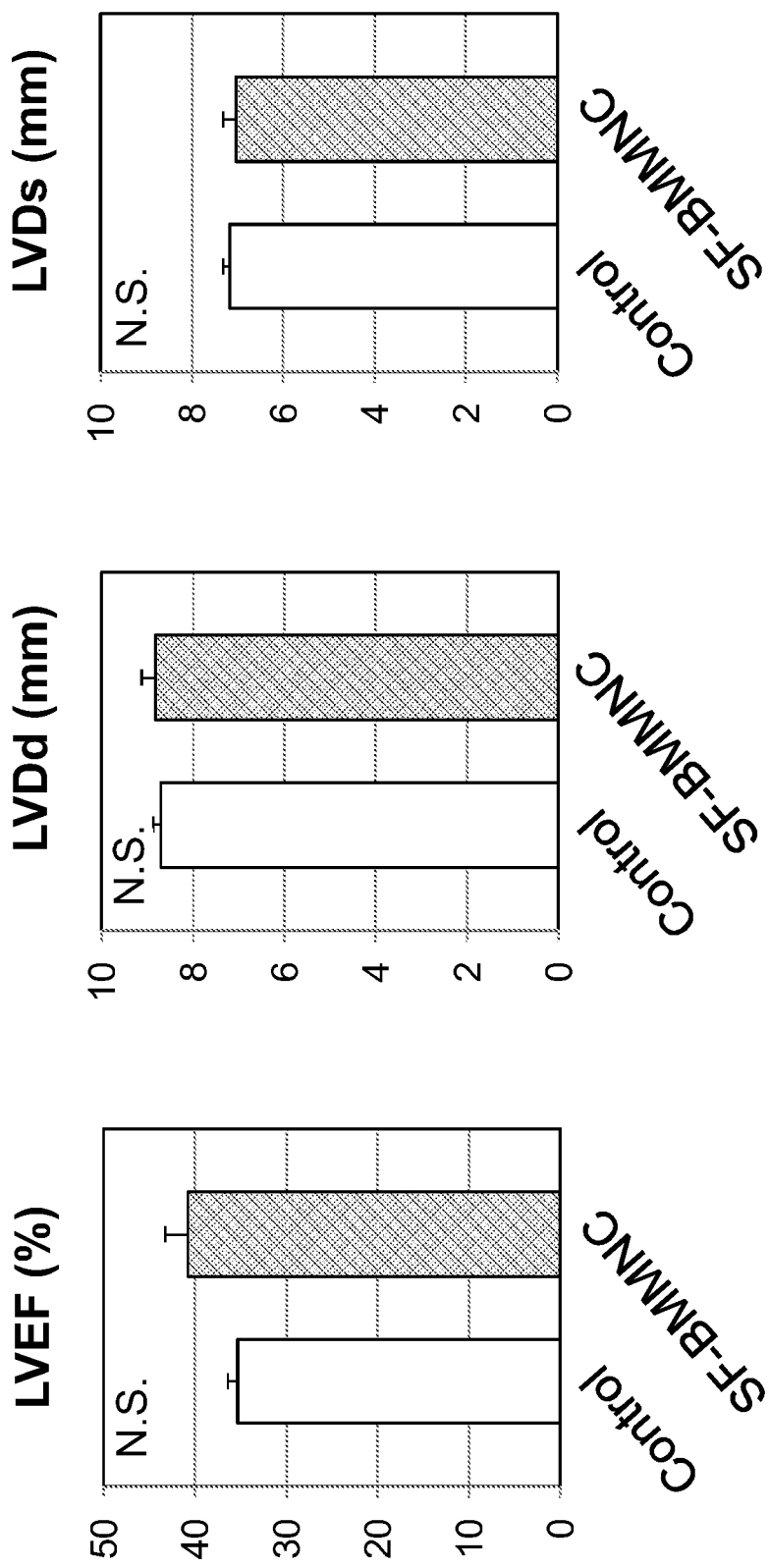
Figure 3:
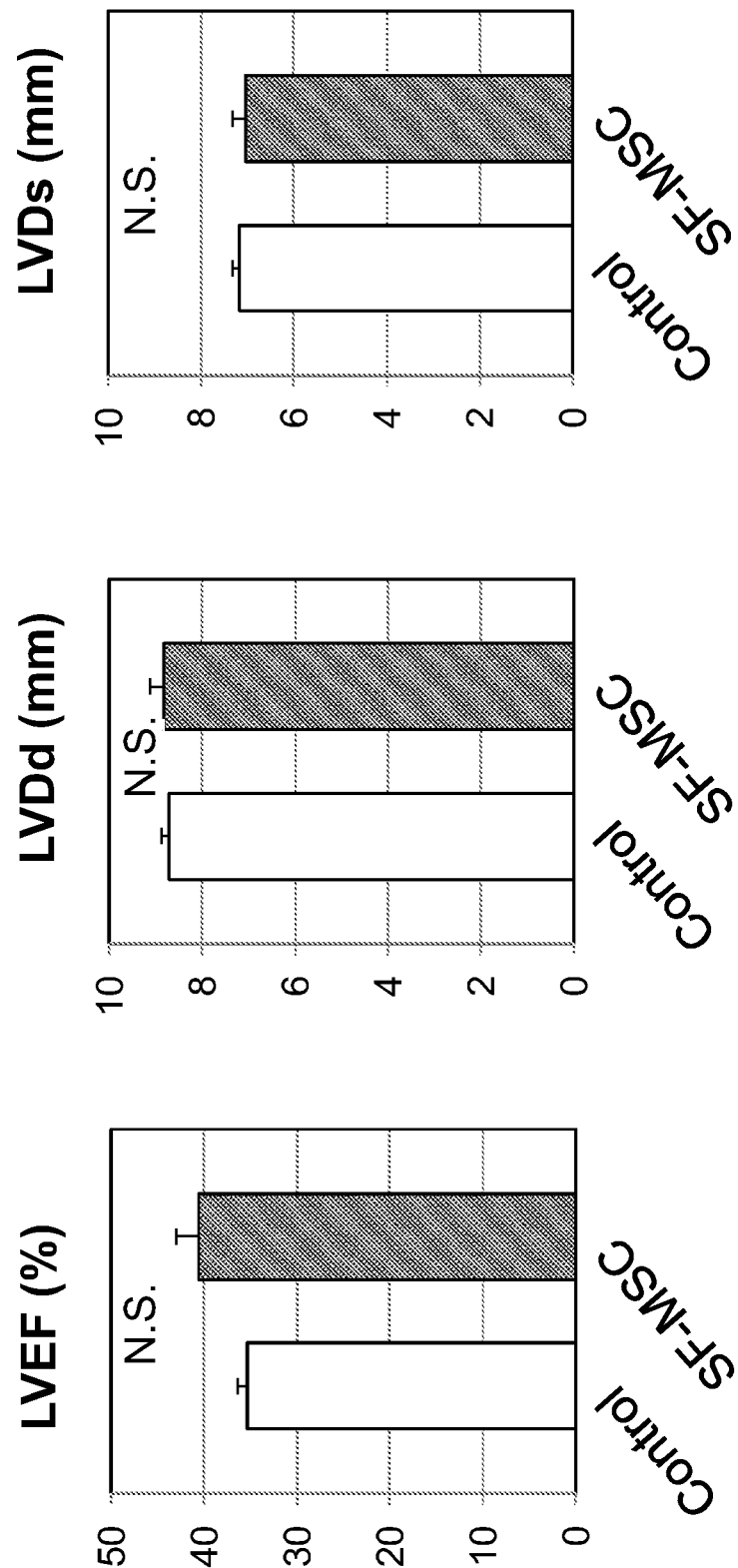
Figure 4:
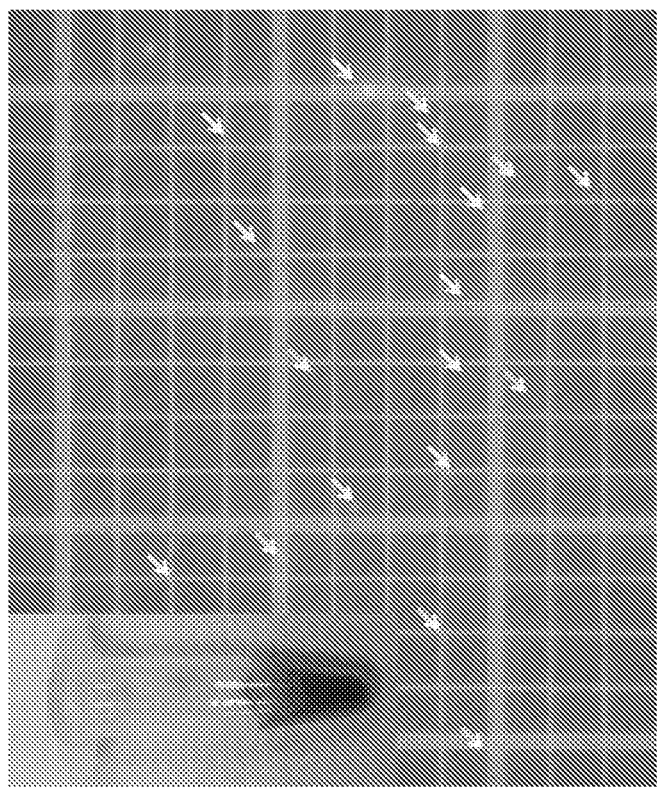
Figure 4:
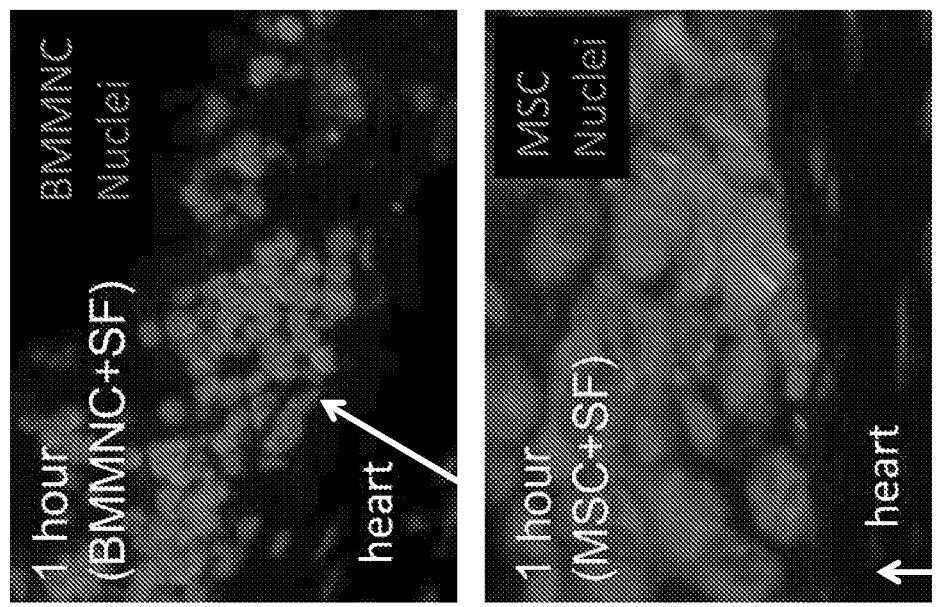

However, this method using either cell type did not achieve significantly-improved cardiac function at Day 28 (measured by echocardiography) compared to sham-treatment group (FIGS. 2 and 3). In addition, it was found that a certain amount of donor cells retained on the heart surface 1 hour after transplantation (FIGS. 4a and 4b), whilst sizeable numbers of donor cells were observed in the pericardial cavity. This result suggests that Seprafilm® could not retain donor cells sufficiently on the heart surface and that considerable numbers of transplanted cells were released/dropped off from the heart (FIG. 4c).

EXAMPLE 2: PREPARATION OF MULTILAYER MATRIX CONTAINING CELLS (CELL-DRESSING)

Figure 5:
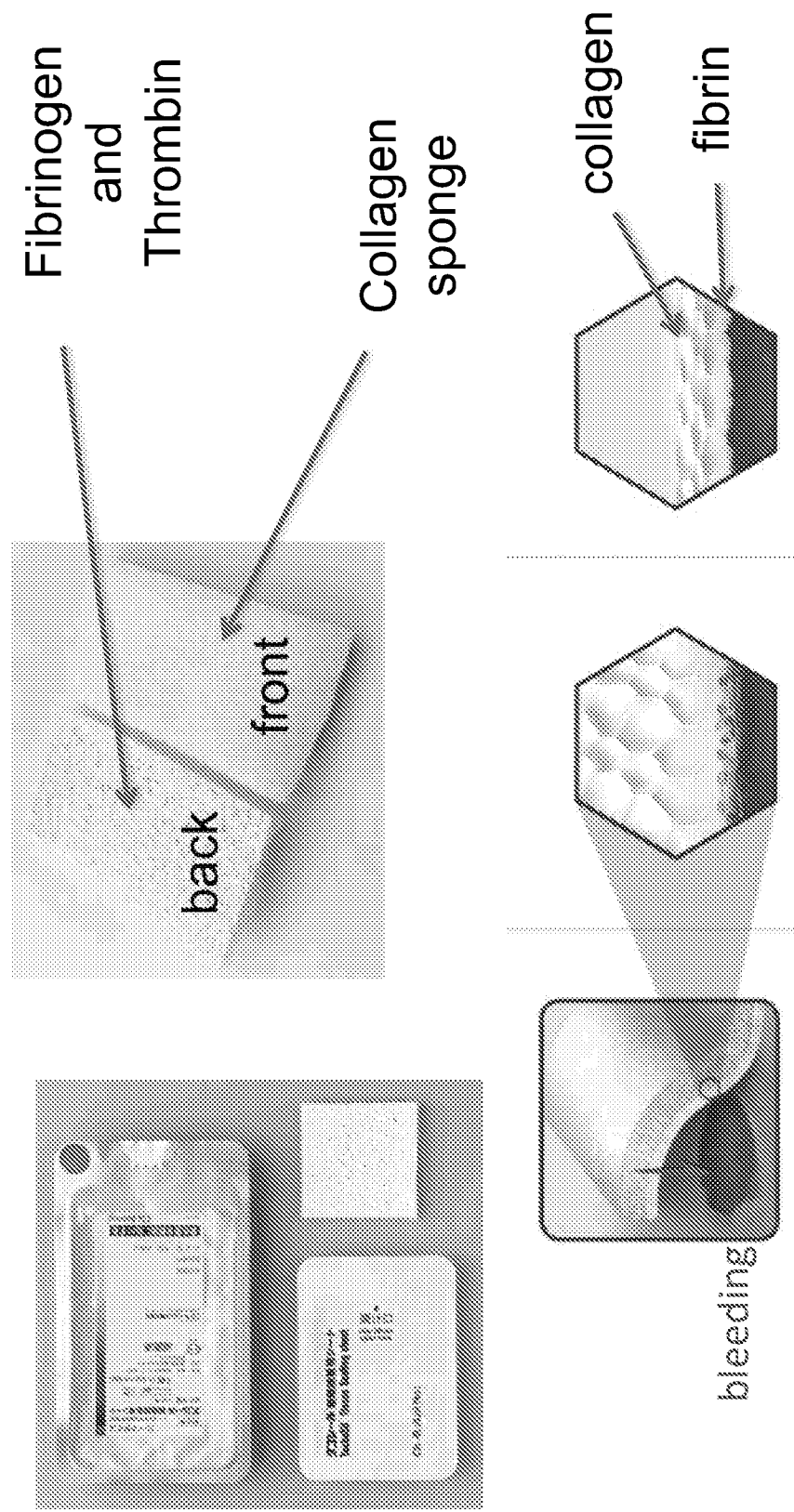
FIG. 5 shows the structure of a TachoSil® (multi-layered fibrin sealant patch).

To solve the issues of a monolayer matrix-aided epicardial placement (Example 1), we invented the use of two-layered (histocompatible and bioresorbable) matrix. TachoSil® (produced by TAKEDA/Nycomed; sold by TAKEDA/Baxter/CSL Behring) is an example of such a two-layered matrix (FIG. 5). The front layer of the matrix consists of a collagen sponge, while the back face includes powdered fibrinogen and thrombin. As soon as a cell suspension was dropped onto the back face, fibrinogen and thrombin reacted to produce fibrin, which offers a comfortable scaffold for the donor cells to retain and settle. Fibrin is quite sticky, and thus can adhere to the heart surface firmly without any suture. The front layer of the collagen sponge supports the fibrin-stem cell complex so that the final product of the matrix incorporating stem cells can be easily handled. This layer is also useful to prevent transplanted stem cells from mechanical stress from outside of the heart (i.e. rubbing of the cells by the lung, pericardium, and chest walls).

Currently, TachoSil® is widely used for a different purpose (haemostasis during surgery including cardiac operation). Topical placement and oppression of this product is effective to stop minor bleeding which is not controllable by surgical procedures. Safety of this product in patients has been proven.

EVARREST® (produced by Ethicon; sold by Ethicon/Omrix Biopharmaceuticals N.V.) is also an example of such a multilayer matrix. EVARREST® is an oxidized regenerated cellulose and vicryl mesh (made from polylactic acid and poly glycolic acid) supported fibrin patch and is commercially available as a pharmaceutical product. The front layer of the matrix consists of an oxidized regenerated cellulose and vicryl mesh, while the back face includes powdered fibrinogen and thrombin. As soon as a cell suspension was dropped onto the back face, fibrinogen and thrombin reacted to produce fibrin, which offers a comfortable scaffold for the donor cells to retain and settle. Fibrin is quite sticky, and thus can adhere to the heart surface firmly without any suture. The front layer of the oxidized regenerated cellulose and vicryl mesh supports the fibrin-stem cell complex so that the final product of the matrix incorporating stem cells can be easily handled. This layer is also useful to prevent transplanted stem cells from mechanical stress from outside of the heart (i.e. rubbing of the cells by the lung, pericardium, and chest walls). Currently, EVARREST® is widely used for a different purpose (haemostasis during surgery including cardiac operation). Topical placement and oppression of this product is effective to stop minor bleeding which is not controllable by surgical procedures. Safety of this product in patients has been proven.

EXAMPLE 3: OPTIMISATION OF MANUFACTURING MSC-TACHOSIL® COMPLEX IN VITRO

We optimised the protocols to produce a TachoSil®-MSC complex. A cell pellet was generated by centrifuging MSC suspensions. The pellet was dissolved in different volumes of ordinary solution (i.e. HBSS or PBS) to make appropriate cell suspensions (FIG. 6).

Figure 6:
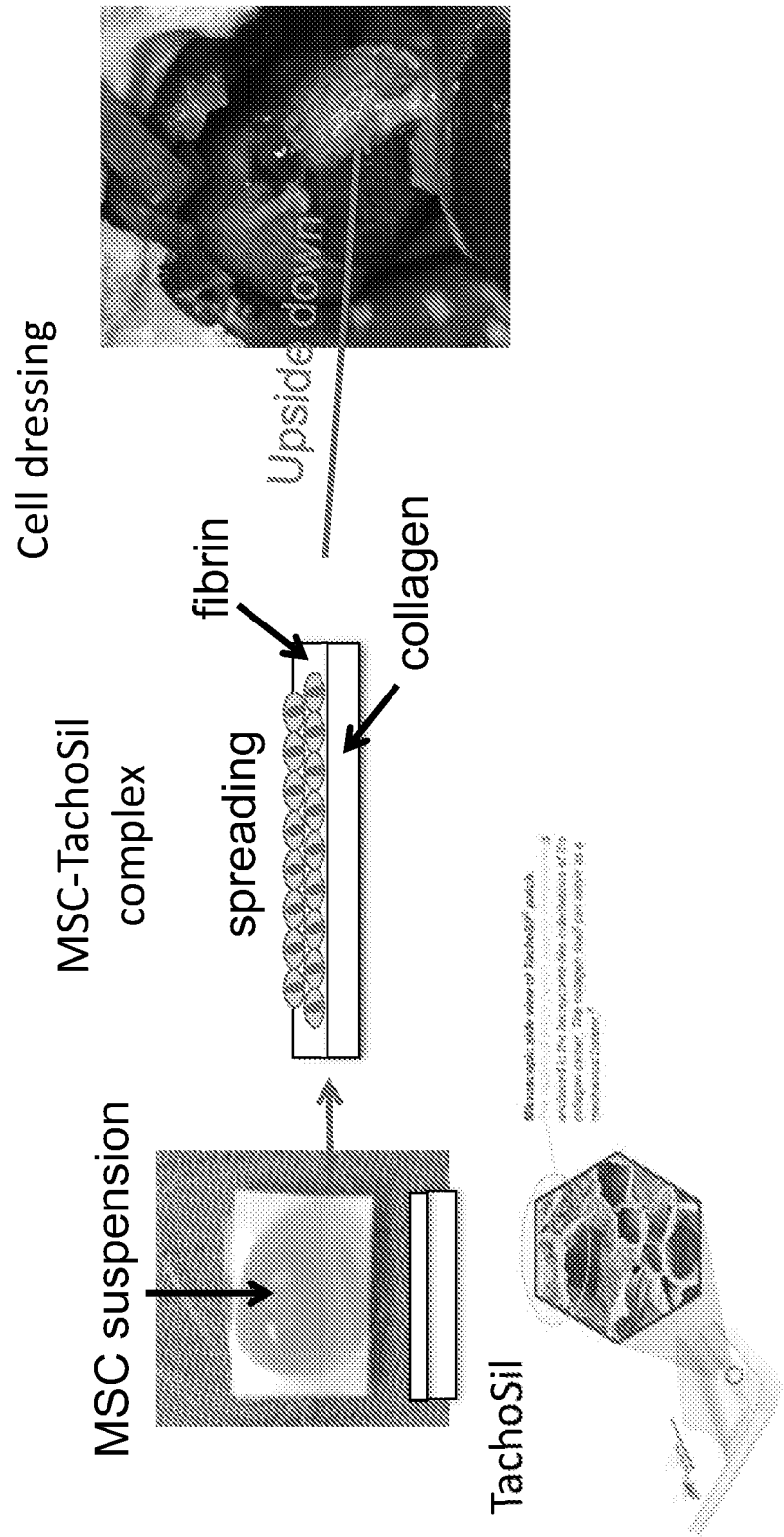
FIG. 6 shows the method for TachoSil®-aided epicardial placement of stem cells.

The cell suspension was gently dropped onto a 1 cm² TachoSil® (fibrin side) and spread on the surface using a pipette tip or cell-scraper (FIG. 6). This was turned upside down and placed onto a plastic culture dish. Too small volume cannot make a homogenous fibrin layer, while too much volume resulted in leakage of MSCs from the TachoSil® when turned upside down.

Results of these experiments showed that approximately 30 (±10) μL MSC suspension per 1 cm² TachoSil® is the optimal condition for the production of the multilayer matrix or cell-dressing. This protocol resulted in appropriate homogeneous fibrin production throughout the TachoSil® incorporation/accommodation of donor MSCs in fibrin, and no leakage was observed when turned upside down.

EXAMPLE 4: IN VIVO TRIAL AND OPTIMISATION OF EPICARDIAL CELL PLACEMENT USING TACHOSIL®

TachoSil® is a commercially-available two-layer matrix, which is clinically approved to use for haemostasis during surgery. The present inventors have found that this product is suitable for use in a cell-dressing therapy for the treatment of heart diseases as described herein and also for other treatments of lesions or trauma as described herein.

TachoSil® is easy-to handle (soft and easily-cut by scissors). Upon placing a cell suspension on the fibrin glue powder, the fibrinogen/thrombin side becomes wet, generating adhesive fibrin. This holds donor cells and also enables the product to adhere to the heart surface without any suture. In addition to these effects, this method has many advantages as a material to aid epicardial placement of stem cells including potential to prevent post-surgical pericardial adhesion (fibrin is a major player in formation of post-operative adhesions) and to improve functionality/survival of the donor stem cells (FIG. 6).

A 200 g rat was anaesthetised, and the heart (epicardium) was exposed through left thoracotomy with opening the pericardium. The left coronary artery was ligated with an 8-0 suture to induce myocardial infarction. After confirmation of the infarction by changes in the ventricular colour and motion (1 hour after ligation), one million rat fetal membrane-derived MSCs dissolved in 30 μL HBSS was spread on a 1 cm² TachoSil® to produce MSC-TachoSil® complex. This was placed onto the epicardial heart surface (targeting ischaemic areas) with the fibrin/MSC side directly contacting to the heart surface (FIG. 6). For accurate and easy placement, MSC-TachoSil® was cut into 3 pieces before placement. To augment the attachment of the MSC-TachoSil® complex on the heart, the complex was gently and lightly oppressed (no leakage of cell suspension or adverse cardiac event occurred). All the procedures were straightforward and the MSC-TachoSil® complex was firmly fixed on the beating heart.

At Day 5 after TachoSil®-MSC placement, TachoSil®-MSC complex was found to be firmly adhered to the heart surface (FIG. 8).

EXAMPLE 5: IN VIVO PROOF-OF-CONCEPT DATA IN A RAT ACUTE MYOCARDIAL INFARCTION MODEL

One million rat fetal membrane-derived MSCs dissolved in 30 μL HBSS was spread on a 1 cm² TachoSil® to produce MSC-TachoSil® complex. A 200 g rat was anaesthetised, and the heart (epicardium) was exposed by left thoracotomy with opening the pericardium. The left coronary artery was ligated with an 8-0 suture to induce myocardial infarction.

After confirmation of the infarction by changes in the ventricular colour and motion (1 hour after ligation), the MSC-TachoSil® was placed onto the epicardial heart surface (targeting ischaemic areas) with the fibrin/MSC side directly contacting to the heart surface. For accurate and easy placement, MSC-TachoSil® was cut into 3 pieces before placement. To augment the attachment of the MSC-TachoSil® complex on the heart, the complex was gently and lightly oppressed (no leakage of cell suspension or adverse cardiac event occurred).

For the control group, myocardial infarction was caused but no treatment was added. The chest was closed and the rat was returned to the normal cage.

All the procedures were straightforward and the MSC-TachoSil® complex was firmly fixed on the beating heart. Throughout the post-treatment days studied, there was no adverse event observed (in terms of rat mortality, general behaviour, food intake, body weight changes).

At 4 weeks post-treatment, echocardiography demonstrated that left ventricular ejection fraction (=LVEF, an indicator of global cardiac function) was significantly improved in the TS group (MSC-TachoSil® treatment) compared to the Control group (FIG. 7; n=7 in each group). Post-myocardial infarction cardiac dilatation (LVDs=left ventricular systolic dimension) was attenuated. There was a tendency of reduction of diastolic cardiac size (LVDd=left ventricular diastolic dimension), but this was not statistically significant (p=0.0979).

The MSC-TachoSil® complex was not clearly detected by direct vision at Day 28 (FIG. 9), suggesting the most of TachoSil® had been degraded and absorbed by this time. No adverse event such as fluid collection or post-operative pericardial adhesion was observed, demonstrating the safety of the treatment.

Immunohistological analysis demonstrated a great retention and survival of donor cells (MSCs were labelled with an orange fluorescent dye before transplantation) on the surface of the heart at Day 7 and 28 post-treatment (FIGS. 10 and 11). The majority of MSCs were retained on the heart surface.

EXAMPLE 6: IN VIVO PROOF-OF-CONCEPT DATA OF EPICARDIAL CELL PLACEMENT USING TACHOSIL® IN A RAT POST MYOCARDIAL INFARCTION ISCHAEMIC CARDIOMYOPATHY MODEL

Four weeks after induction of myocardial infarction by left coronary artery ligation in rat, TachoSil® (1 cm$^2$) mixed with different numbers (0.5, 1, 2, 4×10$^6$ cells respectively) of rat fetal membrane-derived MSCs dissolved in 30 µL HBSS (TS+MSC group), TachoSil® only (TS only group), or nothing (Sham group) was placed onto the epicardial heart surface (targeting ischaemic areas) with the fibrin/MSC side directly contacting to the heart surface (FIG. 6). For accurate and easy placement, MSC-TachoSil® was cut into 3 pieces before placement. All the procedures were straightforward and the MSC-TachoSil® complex was firmly fixed on the beating heart.

Four weeks after treatment, echocardiography (FIG. 12 upper panels) and cardiac catheterisation (FIG. 12 lower panels) demonstrated that epicardial placement of the MSC-TachoSil® complex improved cardiac function and structure in proportion to the cell numbers. Functional improvement by intramyocardial injection (IM) occurred to a lesser extent compared to the TachoSil-aided placement of the same number of MSCs.

Four weeks after treatment, TS+MSC group showed significantly attenuated pathological fibrosis (FIG. 13A), reduced cardiomyocyte hypertrophy (FIG. 13B; WGA=Wheat germ agglutinin), and improved microvascular formation (FIG. 13C) in both remote and border areas of myocardial infarction, compared to both Sham and TS only groups.

EXAMPLE 7: EVALUATION OF SURVIVAL RATE OF THE CELLS APPLIED TO MULTILAYER MATRIX

Human amnion-derived MSCs were obtained in the following steps. The fetal appendage (amnion) was aseptically collected from pregnant patients with informed consent. The resulting amnion and was placed in a sterile vat containing physiological saline solution. Amnion was washed with Hanks' balanced salt solution (Ca·Mg-free) to remove the adhered blood and clots. 240 PU/mL collagenase and 200 PU/mL dispase I were added to the amnion, and stirred under conditions of 50 rpm for 90 min at 37° C. The resulting cell suspension containing amnion MSC was filtered with nylon mesh filter (pore size: 95 µm) and remaining undigested amnion was removed. A cell population containing amnion MSC obtained above were cultured in Cell Stack (6,000 cells/cm$^2$) with αMEM containing 10% FBS until cells were being subconfluent. Then, cells were treated with TrypLE Select and were detached from the Cell Stack. The resulting cell suspension was cultured in αMEM containing 10% FBS with cell density of 6,000 cells/cm$^2$. This cell culture and passage were repeated 5 times (totally 6 passage).

6 passaged human amnion-derived MSCs obtained in the above procedure were suspended in a mixed solution (CP-1 solution) of a saline containing 5 wt % DMSO, 6 wt % hydroxyethyl starch, 4% human serum albumin and 50 wt % PRM11640 at a density of 8×10$^7$-cells/mL, and were frozen and stored in a liquid nitrogen. It can be suitably used as amniotic MSC drugs. After thawing of this drug, 30 µL (2.4×10$^6$ cells) were collected and were spread on fibrin layer of TachoSil® (1 cm$^2$) to prepare TachoSil®-MSC complex. Then, MSC TachoSil®-MSC complex was applied to 12 well plate containing RPM11640 (200 µL), so that the fibrin layer is upper. The 12 well plate was covered with a lid, and left to stand at 37° C. After 3, 6 and 10 hours, TachoSil®-MSC complex which was taken out from the 12 well plate was added to Eppendorf tube containing saline (500 µL) added with 10 IU/mL nattokinase, and was incubated at 37° C. for 10 minutes to release the cells. TachoSil® was removed from the Eppendorf tube, and PRM11640 (500 µL) was added. Then, the tube was centrifuged at 400 g for 3 minutes, and the supernatant was removed. Further, PRM11640 was added to prepare a cell suspension (100 µL) of 1×10$^6$ cells/mL, and PRM11640 was added in the same way to prepare a cell suspension (100 µL) of 1×10$^6$ cells/mL. 7-AAD (Via Probe™, BD bioscience) (10 µL) was added thereto, and the cell suspension was left stand at dark place for 15 minutes. Then, 7-AAD positive ratio (death cell ratio) of (A) the cell immediately after thawing and (B) the cells after preparation of TachoSil®-MSC complex was measured by using flow cytometer. The cell survival ratio was calculated by the following formula from the obtained values. As a result, the cell survival ratios after 3, 6, and 10 hours were 95%, 96%, and 92% respectively. (the cell survival ratio)= [100−(7-AADpositive ratio of (B))%/(100−(7-AAD positive rate of (A))%]

These results showed Tachosil® could retain cells with a high cell viability. Therefore, fibrinogen/thrombin can be preferably used as a bioadhesive material and collagen can be preferably used as a bioresorbable material.

EXAMPLE 8: IN VIVO FEASIBILITY DATA OF EPICARDIAL CELL PLACEMENT USING TACHOSIL® IN A PIG MODEL

Two pieces of TachoSil® (25 cm$^2$) mixed with 1 mL of 5×10$^7$ cells/mL pig bone marrow-derived MSCs were placed on to the surface of the beating heart of pigs (20-22 kg) through thoracotomy under general anaesthesia and mechanical ventilation.

In addition to the technical feasibility, great retention and survival of MSCs (labelled orange with CM-DiI) was histologically confirmed at Day 1 (FIG. 14). The TachoSil®-MSC complex strongly adhered to the heart surface. Also, no acute adverse event, including arrhythmia occurrence and immunological reaction, was observed in these studies.

Histological analysis demonstrated a great retention and survival of donor cells (MSCs were labelled with an orange fluorescent dye before transplantation) on the surface of the heart at day 1 (FIG. 14). The majority of MSCs retained on the heart surface. Scale bar=100 µm.

In the previous experiments in a large animal model (using a hydrogel-aided epicardial placement), it has been revealed that mechanical rubbing is the major problem for the donor cells to be retained on the heart surface. The multilayer matrix of this invention enabled successful epicardial placement of stem cells onto the heart surface (as below), which could not be achieved using other films such as a monolayer film, Seprafilm®, Integran®, Gelfoam® and INTEGRAN®.

Gelfoam® (produced by Pfizer) is an example of a bioadhesive material. Gelfoam® is a sterile compressed sponge made from gelatine and is commercially available as a medical product. Currently, this commercial product is widely used for a different purpose (hemostatic). Safety of this product in patients has been proven.

Integran® (produced by Koken) is an example of a bioresorbable material. Integran® is a topical hemostat sheet made from collagen and is commercially available as a medical product. Currently, this commercial product is widely used for a different purpose (hemostatic). Safety of this product in patients has been proven.

INTERCEED® (produced by Ethicon) is an example of a bioresorbable material. INTERCEED® is an anti-adhesion sheet made of regenerated oxidized cellulose and is commercially available as a medical product. Currently, this commercial product is widely used for a different purpose (post-operative adhesion prevention). Safety of this product in patients has been proven.

EXAMPLE 9: IN VIVO FEASIBILITY DATA OF EPICARDIAL CELL PLACEMENT USING TACHOSIL® IN A PIG MODEL

Two pieces of TachoSil® (25 cm$^2$) mixed with 1 mL of $8\times10^7$ cells/mL human amnion-derived MSC drug which were obtained according to example 7, were placed on to the surface of the beating heart of pigs (20-22 kg) through thoracotomy under general anaesthesia and mechanical ventilation.

In addition to the technical feasibility, great retention and survival of MSCs (labelled orange with CM-DiI) was histologically confirmed at Day 1 (FIG. 15). The TachoSil®-MSC complex strongly adhered to the heart surface.

Histological analysis demonstrated a great retention and survival of donor cells (MSCs were labelled with an orange fluorescent dye before transplantation) on the surface of the heart at Day 1 (FIG. 15). The majority of MSCs were retained on the heart surface. Scale bar=400 µm.

No acute adverse event, including arrhythmia occurrence and immunological reaction, did not occur as far as we studied.

With regard to the used human amnion-derived MSCs, the ratio of cells exhibiting positive to the surface antigens (CD73, CD90, CD105, CD34, CD45, CD106, and CD142) was analyzed as follows, under measurement conditions, the number of cells to be analyzed was 10,000 cells, and a flow rate setting of "Slow" (14 µL/min), using BD Accuri™ C6 Flow Cytometer manufactured by Becton, Dickinson and Company (BD).

(1) The measurement results were shown in the form of a histogram, in which the longitudinal axis indicates the number of cells and the horizontal axis indicates the fluorescence intensity of an antibody labeling dye.

(2) The fluorescence intensity, at which a cell population with stronger fluorescence intensity accounts for 0.1% to 1.0% of all of the cells measured with the antibody used as an isotype control, was determined.

(3) The ratio of cells having fluorescence intensity higher than the fluorescence intensity determined in (2) above to all of the cells measured with antibodies against various types of antigens was calculated.

As a result, the CD73-positive rate was 50% or more (specifically, 100%), the CD90-positive rate was 50% or more (specifically, 100%), the CD105-positive rate was 50% or more (specifically, 99%), the CD34-positive rate was less than 5% (specifically, 0%), the CD45-positive rate was less than 5% (specifically, 1%), the CD106-positive rate was less than 5% (specifically, 0%), and the CD142-positive rate was 50% or more (specifically, 98%). In the present measurement, as isotype control antibodies, PE Mouse IgG1, κ Isotype Control (BD/model number: 555749), FITC Mouse IgG1, κ Isotype Control (BD/model number: 550616), FITC Mouse IgG2a, κ Isotype Control, REA Control (S)-PE isotype control antibody (Miltenyi Biotec/130-104-612) were used. As an antibody against the CD73 antigen, PE Mouse Anti-Human CD73 (BD/model number: 550257) was used; as an antibody against the CD90 antigen, FITC Mouse Anti-Human CD90 (BD/model number: 555595) was used; as an antibody against the CD105 antigen, Anti-Human Antibodies FITC Conjugate (AnCell/model number: 326-040) was used; as an antibody against the CD34 antigen, PE Mouse Anti-Human CD34 (BD/model number: 343505) was used; as an antibody against the CD45 antigen, FITC Mouse Anti-Human CD45 (BD/model number: 555482) was used; as an antibody against the CD106 antigen, CD106-PE, human monoclonal (Miltenyi Biotec/130-104-163) was used; and as an antibody against the CD142 antigen, PE Mouse Anti-Human CD142 (BD/model number: 561713) was used.

EXAMPLE 10: EVALUATION OF SURVIVAL RATE OF THE HUMAN AMNION-DERIVED MSCS APPLIED TO MULTILAYER MATRIX

Human amnion-derived MSCs which were obtained according to example 7, were suspended in a mixed solution (CP-1 solution) of a saline containing 5 wt % DMSO, 6 wt % hydroxyethyl starch, 4% human serum albumin and 50 wt % PRMI1640 at a density of $1\times10^7$ cells/mL, were frozen and stored in a liquid nitrogen. After thawing, 30 µL ($0.3\times10^6$ cells) were collected and were spread on fibrin layer of TachoSil® (1 cm$^2$) to prepare TachoSil®-MSC complex. Then, MSC TachoSil®-MSC complex was applied to 12 well plate containing RPMI1640 (200 µL), so that the fibrin layer is upper. The 12 well plate was covered with a lid, and left to stand at 37° C. After 3, 6 and 10 hours, TachoSil®-MSC complex which was taken out from the 12 well plate was added to Eppendorf tube containing saline (500 µL) added with 10 IU/mL nattokinase, and was incubated at 37° C. for 10 minutes to release the cells. TachoSil® were removed from the Eppendorf tube, and PRMI1640 (500 µL) was added. Then, the tube was centrifuged at 400 g for 3 minutes, and the supernatant was removed. Further, PRM11640 was added to prepare a cell suspension (100 μL) of 1×10⁶ cells/mL, and PRM11640 was added in the same way to prepare a cell suspension (100 μL) of 1×10⁶ cells/mL. 7-AAD (Via Probe™, BD bioscience) (10 μL) was added thereto, and the cell suspension was left stand at dark place for 15 minutes. Then, 7-AAD positive ratio (death cell ratio) of (A) the cell immediately after thawing and (B) the cells after preparation of TachoSil®-MSC complex was measured by using flow cytometer. The cell survival ratio was calculated by the following formula from the obtained values. As a result, the cell survival ratios after 3, 6, and 10 hours were 96%, 82%, and 83% respectively. (the cell survival ratio)= [100−(7-AADpositive ratio of (B))%/(100−(7-AAD positive rate of (A))%]

EXAMPLE 11: IN VIVO PROOF-OF-CONCEPT DATA OF EPICARDIAL CELL PLACEMENT USING TACHOSIL® IN A RAT POST MYOCARDIAL INFARCTION ISCHAEMIC CARDIOMYOPATHY MODEL

Human amnion-derived MSCs were suspended in a mixed solution (CP-1 solution) of a saline containing 5 wt % DMSO, 6 wt % hydroxyethyl starch, 4% human serum albumin and 50 wt % PRM11640 at a density of 8×10⁷ cells/mL, were frozen and stored in a liquid nitrogen. Just after thawing, 25 μL (2×10⁶ cells) were collected and were spread on fibrin layer of TachoSil® (1 cm²) to prepare TachoSil®-MSC complex. TachoSil®-MSC complex (TS+ MSC group) or nothing (Sham group) was placed onto the epicardial heart surface (targeting ischaemic areas) with the fibrin/MSC side directly contacting to the heart surface of rat which has been passed four weeks after induction of myocardial infarction by left coronary artery ligation. For accurate and easy placement, MSC-TachoSil® was cut into 3 pieces before placement. All the procedures were straightforward and the MSC-TachoSil® complex was firmly fixed on the beating heart. Four weeks after treatment, echocardiography and cardiac catheterisation demonstrated that epicardial placement of the MSC-TachoSil® complex improved cardiac function and structure compared to the sham group. TS+MSC group showed approximately 10% increase in LVEF. With regard to the used human amnion-derived MSCs, the ratio of cells exhibiting positive to the surface antigens (CD73, CD90, CD105, CD34, CD45, CD106, and CD142) was analyzed as follows, the CD73-positive rate was 50% or more (specifically, 100%), the CD90-positive rate was 50% or more (specifically, 100%), the CD105-positive rate was 50% or more (specifically, 100%), the CD34-positive rate was less than 5% (specifically, 0%), the CD45-positive rate was less than 5% (specifically, 0%), the CD106-positive rate was less than 5% (specifically, 1%), and the CD142-positive rate was 50% or more (specifically, 95%).

EXAMPLE 12: IN VIVO FEASIBILITY DATA OF EPICARDIAL CELL PLACEMENT USING INTEGRAN®-GELFOAM® MATRIX IN A PIG MODEL 9 cm² of Integran® (as a bioresorbable material) was put on the 9 cm² of Gelfoam® (as a bioadhesive material), and their four corners were fixed with suture thread. Then, 1 mL of 8×10⁷ cells/mL human amnion-derived MSC drug which were obtained according to example 7 (but the donor amnion was different from example 7), was put on the Gelfoam® side and this was placed on to the surface of the beating heart of pigs (20-22 kg) through thoracotomy under general anaesthesia and mechanical ventilation.

In addition to the technical feasibility, great retention and survival of MSCs (labelled orange with CM-DiI) was histologically confirmed at Day 1 (FIG. 16). The Integran®-Gelfoam®-MSC complex strongly adhered to the heart surface. Also, no acute adverse event, including arrhythmia occurrence and immunological reaction, did not occur as far as we studied.

Histological analysis demonstrated a great retention and survival of donor cells (MSCs were labelled with an orange fluorescent dye before transplantation) on the surface of the heart at day 1 (FIG. 16). The majority of MSCs were retained on the heart surface. Scale bar=400 μm.

Human amnion MSC drug used for the in vivo study was obtained from a different donor from Example 7. The ratio of cells exhibiting positive to the surface antigens (CD73, CD90, CD105, CD34, CD45, CD106, and CD142) was analyzed according to example 7.

As a result, the same characteristics as the donor in Example 7 were observed. The CD73-positive rate was 50% or more (specifically, 100%), the CD90-positive rate was 50% or more (specifically, 100%), the CD105-positive rate was 50% or more (specifically, 99%), the CD34-positive rate was less than 5% (specifically, 0%), the CD45-positive rate was less than 5% (specifically, 0%), the CD106-positive rate was less than 5% (specifically, 1%), and the CD142-positive rate was 50% or more (specifically, 95%). In the present measurement, as isotype control antibodies, PE Mouse IgG1, κ Isotype Control (BD/model number: 555749), FITC Mouse IgG1, κ Isotype Control (BD/model number: 550616), FITC Mouse IgG2a, κ Isotype Control, REA Control (S)-PE isotype control antibody (Miltenyi Biotec/ 130-104-612) were used. As an antibody against the CD73 antigen, PE Mouse Anti-Human CD73 (BD/model number: 550257) was used; as an antibody against the CD90 antigen, FITC Mouse Anti-Human CD90 (BD/model number: 555595) was used; as an antibody against the CD105 antigen, Anti-Human Antibodies FITC Conjugate (AnCell/ model number: 326-040) was used; as an antibody against the CD34 antigen, PE Mouse Anti-Human CD34 (BD/model number: 343505) was used; as an antibody against the CD45 antigen, FITC Mouse Anti-Human CD45 (BD/model number: 555482) was used; as an antibody against the CD106 antigen, CD106-PE, human monoclonal (Miltenyi Biotec/ 130-104-163) was used; and as an antibody against the CD142 antigen, PE Mouse Anti-Human CD142 (BD/model number: 561713) was used.

Also, the survival rate of the cells applied to Integran®-Gelfoam® matrix was evaluated according to example 7. As a result, the cell survival ratios after 3, 6, and 10 hours were 97%, 95%, and 90% respectively.

These results showed the great adhesion ability of Integran®-Gelfoam® matrix to biological tissues, as well as Tachosil®, and Integran®-Gelfoam® matrix could retain cells with a high cell viability. As described above, the use of a monolayer film such as Gelfoam® and Integran® resulted in unsuccessful epicardial placement of stem cells onto the pig heart surface, however, Integran®-Gelfoam® matrix which is made by combining these monolayer films to form a multi-layer matrix achieved great retention of stem cells onto the pig heart surface. As the results of this example, the multilayer matrix made of collagen and gelatin layer containing cells can be preferably used as drugs for heart diseases such as ischemic cardiomyopathy.

EXAMPLE 13: IN VIVO FEASIBILITY DATA OF EPICARDIAL CELL PLACEMENT USING INTERCEED®-GELFOAM® IN A PIG MODEL 9 cm² of INTERCEED® (as a bioresorbable material) was put on the 9 cm² of Gelfoam® (as a bioadhesive material), and their four corners were fixed with suture thread. Then, 1 mL of 8×10⁷ cells/mL human amnion-derived MSC drug (amnion donor was same as example 12) which were obtained according to example 12, was put on the Gelfoam® side and this was placed on to the surface of the beating heart of pigs (20-22 kg) through thoracotomy under general anaesthesia and mechanical ventilation.

In addition to the technical feasibility, great retention and survival of MSCs (labelled orange with CM-Dil) was histologically confirmed at Day 1 (FIG. 16). The INTERCEED®-Gelfoam®-MSC complex strongly adhered to the heart surface. Also, no acute adverse event, including arrhythmia occurrence and immunological reaction, did not occur as far as we studied.

Histological analysis demonstrated a great retention and survival of donor cells (MSCs were labelled with an orange fluorescent dye before transplantation) on the surface of the heart at day 1 (FIG. 16). The majority of MSCs were retained on the heart surface. Scale bar=400 µm.

Also, the survival rate of the cells applied to INTERCEED®-Gelfoam® matrix was evaluated according to example 12. As a result, the cell survival ratios after 3, 6, and 10 hours were 95%, 92%, and 90% respectively.

These results showed the great adhesion ability of INTERCEED®-Gelfoam® matrix to biological tissues, as well as Tachosil®, and INTERCEED®-Gelfoam® matrix could retain cells with a high cell viability. As described above, the use of a monolayer film such as INTERCEED® and Gelfoam® resulted in unsuccessful epicardial placement of stem cells onto the pig heart surface, however, Integran®-Gelfoam® matrix which is made by combining these monolayer films to form a multi-layer matrix achieved great retention of stem cells onto the pig heart surface. As the results of this example, the multilayer matrix made from regenerated oxidized cellulose and gelatin layer containing cells can be preferably used as drugs for heart diseases such as ischemic cardiomyopathy.

EXAMPLE 14: EVALUATION OF SURVIVAL RATE OF THE HUMAN ADIPOSE TISSUE-DERIVED MSCS APPLIED TO MULTILAYER MATRIX

Human adipose tissue-derived stem cells (Lonza, PT-5006) were thawed and cultured in a density of 6,000 cells/cm² with aMEM containing 5% human platelet lysate until cells were being subconfluent. Then, cells were treated with TrypLE Select and were detached from the dish and washed with aMEM containing 5% human platelet lysate. The cell suspension was centrifuged and cell pellet was suspended in a mixed solution (CP-1 solution) of a saline containing 5 wt % DMSO, 6 wt % hydroxyethyl starch, 4% human serum albumin and 50 wt % PRM11640 at a density of 8×10⁷ cells/mL, were frozen and stored in a liquid nitrogen. The ratio of cells exhibiting positive to the surface antigens (CD73, CD90, CD105, CD34, CD45, CD106, and CD142) was analyzed according to example 7. As a result, the CD73-positive rate was 50% or more (specifically, 100%), the CD90-positive rate was 50% or more (specifically, 95%), the CD105-positive rate was 50% or more (specifically, 99%), the CD34-positive rate was less than 5% (specifically, 0%), the CD45-positive rate was less than 5% (specifically, 0%). After thawing of this adipose tissue-derived MSC, 30 µL (2.4×10⁶ cells) were collected and were spread on fibrin layer of TachoSil® (1 cm²) to prepare TachoSil®-MSC complex. Then, TachoSil®-MSC complex was applied to 12 well plate containing RPM11640 (200 µL), so that the fibrin layer is upper. The 12 well plate was covered with a lid, and left to stand at 37° C. After 3, 6 and 10 hours, TachoSil®-MSC complex which was taken out from the 12 well plate was added to Eppendorf tube containing saline (500 µL) added with 10 IU/mL nattokinase and was incubated at 37° C. for 10 minutes to release the cells. TachoSil® was removed from the Eppendorf tube, and PRM11640 (500 µL) was added. Then, the tube was centrifuged at 400 g for 3 minutes, and the supernatant was removed. Further, PRM11640 was added to prepare a cell suspension (100 µL) of 1×10⁶ cells/mL, and PRM11640 was added in the same way to prepare a cell suspension (100 µL) of 1×10⁶ cells/mL. 7-AAD (Via Probe™, BD bioscience) (10 µL) was added thereto, and the cell suspension was left to stand at dark place for 15 minutes. Then, 7-AAD positive ratio (death cell ratio) of (A) the cells just thawed and (B) the cells after preparation of TachoSil®-MSC complex was measured by using flow cytometer. The cell survival ratio was calculated by the following formula from the obtained values. As a result, the cell survival ratios after 3, 6, and 10 hours were 92%, 90%, and 81% respectively. (the cell survival ratio)=[100−(7-AADpositive ratio of (B))%/(100−(7-AAD positive rate of (A))%]

This result indicated that adipose tissue-derived MSCs can also be preferably used with multi-layer matrix.

Also, great therapeutic effect can be expected by applying complex of adipose tissue-derived MSCs and multilayer matrix to the heart, as it is well known that adipose tissue-derived MSC is useful for heart diseases such as ischemic cardiomyopathy (D. Mori et al., Cell Spray Transplantation of Adipose-Derived Mesenchymal Stem Cell Recovers Ischemic Cardiomyopathy in a Porcine Model, *Transplantation* 2018;).

EXAMPLE 15: EVALUATION OF SURVIVAL RATE OF THE HUMAN AMNION-DERIVED MSCS APPLIED TO BESCHITIN®-GELFOAM®

Beschitin® (produced by Nipro) is a wound protective agent made from chitin and is commercially available as a medical product in Japan. 1 cm² of Beschitin® (W-A type as a bioresorbable material) was put on the 1 cm² of Gelfoam® (as a bioadhesive material), and their diagonal two corners were fixed with suture thread. Then, 30 µL of 8×10⁷ cells/mL human amnion-derived MSC drug (amnion donor was same as example 12) which were obtained according to example 12, was put on the Gelfoam® side. Then, the survival rate of the cells applied to Beschitin®-Gelfoam® matrix was evaluated according to example 7. As a result, the cell survival ratios after 3, 6, and 10 hours were 96%, 94%, and 90% respectively. These results showed Beschitin®-Gelfoam® matrix could retain cells with a high cell viability. As the results of this example, the multilayer matrix made from chitin and gelatin layer containing cells can be preferably used as drugs for cell therapies.

EXAMPLE 16: EVALUATION OF SURVIVAL RATE OF THE HUMAN AMNION-DERIVED MSCS APPLIED TO NEOVEIL®-GELFOAM®

NEOVEIL® (produced by Gunze) is a tissue reinforcement agent made from polyglycolic acid and is commercially available as a medical product in Japan. 1 cm² of NEOVEIL® (S type as a bioresorbable material) was put on the 1 cm² of Gelfoam® (as a bioadhesive material), and their diagonal two corners were fixed with suture thread. Then, 30 µL of 8×10⁷ cells/mL human amnion-derived MSC drug (amnion donor was same as example 12) which were obtained according to example 12, was put on the Gelfoam® side. Then, the survival rate of the cells applied to NEOVEIL®-Gelfoam® matrix was evaluated according to example 7. As a result, the cell survival ratios after 3, 6, and 10 hours were 96%, 94%, and 91% respectively. These results showed NEOVEIL®-Gelfoam® matrix could retain cells with a high cell viability. As the results of this example, the multilayer matrix made from polyglycolic acid and gelatin layer containing cells can be preferably used as drugs for cell therapies.

EXAMPLE 17: EVALUATION OF SURVIVAL RATE OF THE HUMAN AMNION-DERIVED MSCS APPLIED TO INTERCEED®-TachoSil®

1 cm² of INTERCEED® (as a bioresorbable material) was put on the 1 cm² of TachoSil® (as a bioadhesive material), and their diagonal two corners were fixed with suture thread. Then, 30 µL of 8×10⁷ cells/mL human amnion-derived MSC drug (amnion donor was same as example 12) which were obtained according to example 12, was put on the fibrinogen-thrombin side of TachoSil®. Then, the survival rate of the cells applied to INTERCEED®-TachoSil® matrix was evaluated according to example 7. As a result, the cell survival ratios after 3, 6, and 10 hours were 96%, 96%, and 93% respectively. These results showed NEOVEIL®-TachoSil® matrix could retain cells with a high cell viability. As the results of this example, the multilayer (three-layer) matrix made from regenerated oxidized cellulose, collagen and fibrinogen layer containing cells can be preferably used as drugs for cell therapies.

SUMMARY

The examples herein show that a cell-dressing multilayer matrix can be prepared which is suitable for the treatment of acute myocardial infarction as well as chronic heart failure. Although monolayer matrix could not achieve this, we found that a two-layer matrix is able to establish epicardial placement of stem cells. Epicardial placement of this composition was feasible and effective to retain and engraft donor cells to the heart. Therapeutic efficacy of this composition was also confirmed in two different heart disease models. Feasibility in a large animal was also confirmed.

This method allows instant and on-site production of a tissue-engineering multilayer matrix, which can be immediately applied to the patient (onto the heart surface). All procedures required for the "cell-dressing" therapy are extremely simple and practical by any ordinary clinician/hospital staff without requirement of specific equipment or expertise. The "cell-dressing" can be generated in a surgical theatre without requirement of any specific equipment such as high-grade cell processing centre, when the donor cells are supplied externally. The whole process for generation/placement will complete in half an hour, causing little additional burden to the clinical staff or to the patients. Thus, it is very easy and reasonable to add this treatment to the routine heart surgery (it is known that cell therapy enhances the effects of coronary artery bypass graft surgery). It is also possible to perform this treatment solely (with open chest procedure or using endoscope and so on).

The invention claimed is:
1. A multilayer matrix comprising at least two layers in which the first layer comprises a bioresorbable material and the second layer comprises a bioadhesive material, wherein the second layer contains cells and said first layer does not contain cells, wherein said bioresorbable material and said bioadhesive material are not the same material, wherein the bioresorbable material is at least one member selected from the group consisting of collagen, cellulose, cellulose acetate, chitosan, chitin, polylactate, hyaluronic acid, and polyglycolic acid, wherein the bioadhesive material is fibrin, and wherein a cell density comprised in the second layer is $2 \times 10^6$ cells/cm² or more,
wherein either
the percentage of cells exhibiting positive to CD105, CD73, and CD90 in the cells is 50% or more, and/or
the percentage of cells exhibiting positive to CD142 in the cells is 50% or more, and/or
the cells are mesenchymal stem cells.
2. The multilayer matrix according to claim 1, wherein the percentage of cells exhibiting positive to CD105, CD73 and CD90 in the cells is 50% or more, and the percentage of cells exhibiting positive to CD45 and CD34 in the cells is 10% or less.
3. The multilayer matrix according to claim 1, wherein the percentage of cells exhibiting positive to CD142 in the cells is 50% or more, and the percentage of cells exhibiting positive to CD106 in the cells is 10% or less.
4. The multilayer matrix according to claim 1, wherein the cells are mesenchymal stem cells.
5. The multilayer matrix according to claim 4, wherein the mesenchymal stem cells are derived from fetal appendage.
6. A method comprising administering the multilayer matrix of claim 1 to a subject having a lesion or trauma, wherein said multilayer matrix is applied to the lesion or trauma.
7. The multilayer matrix according to claim 1, wherein the second layer comprises at least two bioadhesive materials.
8. The multilayer matrix according to claim 1, wherein the second layer further contains dimethyl sulfoxide and albumin.
9. A method for producing the multilayer matrix of claim 1, wherein the method comprises:
A) providing a multilayer matrix comprising at least two layers in which the first layer comprises a bioresorbable material and the second layer comprises a bioadhesive material, wherein said bioresorbable material and said bioadhesive material are not the same material, wherein the bioresorbable material is at least one member selected from the group consisting of collagen, cellulose, cellulose acetate, chitosan, chitin, polylactate, hyaluronic acid, and polyglycolic acid, and wherein the bioadhesive material comprises fibrinogen and thrombin;
B) separately preparing a cell suspension, wherein either
the percentage of cells exhibiting positive to CD105, CD73, and CD90 in the cells is 50% or more, and/or
the percentage of cells exhibiting positive to CD142 in the cells is 50% or more, and/or
the cells are mesenchymal stem cells; and
C) applying the cell suspension to only the second layer of the multilayer matrix to obtain a multilayer matrix which has a cell density comprised in the second layer of $2 \times 10^6$ cells/cm² or more, and
wherein upon application of the cell suspension to only the second layer of the multilayer matrix, a fibrin glue is produced from the fibrinogen and thrombin.

10. The method according to claim 6, wherein the administrating area of the multilayer matrix per body weight is 0.1 cm$^2$/kg or more and 6.0 cm$^2$/kg or less.

11. The method according to claim 6, wherein the subject has heart disease, spinal cord injury or ulcers.

12. A method comprising:
providing a multilayer matrix comprising at least two layers in which the first layer comprises a bioresorbable material and the second layer comprises bioadhesive materials, wherein the bioresorbable material is at least one member selected from the group consisting of collagen, cellulose, cellulose acetate, chitosan, chitin, polylactate, hyaluronic acid, and polyglycolic acid, wherein the bioadhesive materials include fibrinogen and thrombin;
dropping a suspension including mesenchymal cells onto the second layer to react the fibrinogen and the thrombin in the suspension and form a fibrin glue layer on the first layer, the fibrin glue layer comprising fibrin and the mesenchymal cells accommodated in the fibrin, thereby mesenchymal cells-multilayer complex comprising the first layer and the fibrin glue layer is manufactured, wherein a cell density in the fibrin glue layer is $2 \times 10^6$ cells/cm$^2$ or more; and
placing the complex onto a heart surface of a patient with the fibrin glue layer directly contacting to the heart surface.

13. The method of claim 12, wherein the patient is suffering from cardiomyopathy.

14. The method of claim 12, wherein the matrix comprising cells is applied to the patient immediately after the cells are applied to the bioadhesive layer, and without storage.

* * * * *